(12) United States Patent
Amos et al.

(10) Patent No.: US 9,522,211 B2
(45) Date of Patent: Dec. 20, 2016

(54) ANTIMICROBIAL DISPOSABLE ABSORBENT ARTICLES

(71) Applicant: 3M INNOVATIVE PROPERTIES COMPANY, St. Paul, MN (US)

(72) Inventors: David T. Amos, St. Paul, MN (US); Bathsheba E. Chong Conklin, St. Paul, MN (US); Alexis S. Statham, Woodbury, MN (US); Michael J. Svarovsky, Granger, IN (US); Leigh E. Wood, Woodbury, MN (US)

(*) Notice: Subject to any disclaimer, the term of this patent is extended or adjusted under 35 U.S.C. 154(b) by 9 days.

(21) Appl. No.: 14/481,190

(22) Filed: Sep. 9, 2014

(65) Prior Publication Data

US 2015/0010478 A1 Jan. 8, 2015

Related U.S. Application Data

(63) Continuation of application No. 13/820,155, filed as application No. PCT/US2011/051303 on Sep. 13, 2011, now abandoned, which is a continuation-in-part of application No. 12/884,341, filed on Sep. 17, 2010, now abandoned.

(51) Int. Cl.
| | |
|---|---|
| *A61L 15/16* | (2006.01) |
| *A61L 15/20* | (2006.01) |
| *A61L 15/44* | (2006.01) |
| *A61L 15/46* | (2006.01) |
| *A61K 31/60* | (2006.01) |
| *A61L 15/42* | (2006.01) |
| *A61F 13/84* | (2006.01) |

(52) U.S. Cl.
CPC ............ *A61L 15/42* (2013.01); *A61F 13/8405* (2013.01); *A61L 15/20* (2013.01); *A61F 2013/8414* (2013.01); *A61L 2400/00* (2013.01); *Y10T 156/10* (2015.01)

(58) Field of Classification Search
None
See application file for complete search history.

(56) References Cited

U.S. PATENT DOCUMENTS

| | | | |
|---|---|---|---|
| 3,707,148 A * | 12/1972 | Bryce | A61F 13/53 604/360 |
| 3,769,978 A | 11/1973 | DeNight et al. | |
| 3,911,173 A | 10/1975 | Sprague, Jr. | |
| 3,935,862 A | 2/1976 | Kraskin | |
| 4,067,997 A | 1/1978 | Kabara | |
| 4,237,591 A | 12/1980 | Ginocchio | |
| 4,573,986 A | 3/1986 | Minetola et al. | |
| 4,643,181 A | 2/1987 | Brown | |
| 4,655,759 A | 4/1987 | Romans-Hess et al. | |
| 4,676,786 A | 6/1987 | Nishino | |
| 4,678,464 A | 7/1987 | Holtman | |
| 4,722,936 A * | 2/1988 | Jacob | A61K 9/0036 424/430 |
| 4,735,624 A | 4/1988 | Mazars | |
| 4,758,240 A | 7/1988 | Glassman | |
| 4,785,996 A | 11/1988 | Ziecker et al. | |
| 4,795,453 A | 1/1989 | Wolfe | |
| 4,798,604 A | 1/1989 | Carter | |
| 4,824,718 A | 4/1989 | Hwang | |
| 4,842,666 A | 6/1989 | Werenicz | |
| 4,847,088 A | 7/1989 | Blank | |
| 5,030,229 A | 7/1991 | Yang | |
| 5,306,487 A | 4/1994 | Karapasha et al. | |
| 5,514,120 A | 5/1996 | Johnston et al. | |
| 5,550,145 A | 8/1996 | Olund et al. | |
| 5,665,776 A | 9/1997 | Yu et al. | |
| 5,728,446 A | 3/1998 | Johnston et al. | |
| 5,733,272 A | 3/1998 | Brunner et al. | |
| 5,951,993 A | 9/1999 | Scholz et al. | |
| 5,993,840 A | 11/1999 | Fawkes et al. | |
| 6,197,322 B1 | 3/2001 | Dutkiewicz et al. | |
| 6,216,699 B1 | 4/2001 | Cox et al. | |
| 6,284,261 B1 | 9/2001 | Tramontana | |
| 6,284,943 B1 | 9/2001 | Osborn, III et al. | |
| 6,316,019 B1 | 11/2001 | Yang | |
| 6,475,501 B1 | 11/2002 | Kelly et al. | |
| 6,476,104 B1 * | 11/2002 | Nakamura | A61L 15/44 524/530 |

(Continued)

FOREIGN PATENT DOCUMENTS

| | | |
|---|---|---|
| CA | 2443668 | 10/2002 |
| EP | 0 174 152 | 7/1989 |
| EP | 0 391 814 | 10/1990 |
| EP | 0 493 728 | 12/1991 |
| EP | 1992367 | 11/2008 |
| FR | 2082526 | 11/1971 |
| GB | 2017505 | 10/1979 |
| WO | WO 86/01378 | 3/1986 |
| WO | WO 91/11161 | 8/1991 |
| WO | WO 91/12949 | 9/1991 |
| WO | WO 95/00093 | 1/1995 |
| WO | WO 98/09520 | 3/1998 |
| WO | WO 00/71183 | 11/2000 |

(Continued)

OTHER PUBLICATIONS

CAS Registry No. 8001-54-5 (Nov. 16, 1984).*

(Continued)

*Primary Examiner* — Bethany Barham
*Assistant Examiner* — Peter Anthopolos

(57) ABSTRACT

Disposable absorbent articles comprising an absorbent material and an antimicrobial composition are disclosed. The antimicrobial composition includes a carrier comprising fatty alcohol and a poly(alkyleneoxy) polymer, and an antimicrobial agent. The antimicrobial composition may be coated on to component substrates such as nonwovens and films, that are incorporated into disposable absorbent articles, such as disposable infant diapers, adult incontinence articles, feminine hygiene articles such as sanitary napkins, wound dressings, bandages, panty liners and tampons, personal care wipes and household wipes to provide odor control, and control of microbial growth.

17 Claims, 4 Drawing Sheets

(56) References Cited

U.S. PATENT DOCUMENTS

| | | | |
|---|---|---|---|
| 6,703,536 B2 | 3/2004 | Roe et al. | |
| 6,716,441 B1 | 4/2004 | Osborne et al. | |
| 6,767,508 B1 | 7/2004 | Yahiaoui et al. | |
| 6,855,134 B2 | 2/2005 | Brooks | |
| 6,904,865 B2 * | 6/2005 | Klofta | A61F 13/42 116/200 |
| 6,916,480 B2 | 7/2005 | Anderson et al. | |
| 7,005,453 B1 * | 2/2006 | Barney | A61K 31/19 424/175.1 |
| 7,056,404 B2 | 6/2006 | McFall et al. | |
| 7,390,774 B2 | 6/2008 | Ghosh et al. | |
| 7,491,862 B1 * | 2/2009 | Besemer | A61L 15/20 604/359 |
| 2002/0006431 A1 | 1/2002 | Tramontana | |
| 2002/0147433 A1 | 10/2002 | McOsker et al. | |
| 2002/0192287 A1 | 12/2002 | Mooney et al. | |
| 2003/0082219 A1 | 5/2003 | Warren et al. | |
| 2003/0135172 A1 * | 7/2003 | Whitmore | A61F 13/15658 604/359 |
| 2003/0213818 A1 | 11/2003 | Hilvert | |
| 2004/0067252 A1 | 4/2004 | Juppo | |
| 2004/0234561 A1 | 11/2004 | Ansmann et al. | |
| 2004/0234605 A1 | 11/2004 | Cox et al. | |
| 2004/0241216 A1 | 12/2004 | Klun et al. | |
| 2004/0241333 A1 | 12/2004 | Cielenski | |
| 2004/0247655 A1 | 12/2004 | Asmus et al. | |
| 2004/0266302 A1 | 12/2004 | DiSalvo et al. | |
| 2005/0002996 A1 | 1/2005 | Sojka | |
| 2005/0080157 A1 | 4/2005 | Wagener et al. | |
| 2005/0089539 A1 | 4/2005 | Scholz et al. | |
| 2005/0124072 A1 | 6/2005 | Boga et al. | |
| 2005/0226913 A1 | 10/2005 | Bringley et al. | |
| 2005/0249791 A1 | 11/2005 | Hobbs et al. | |
| 2005/0276836 A1 | 12/2005 | Wilson et al. | |
| 2006/0051385 A1 | 3/2006 | Scholz | |
| 2006/0275349 A1 | 12/2006 | Andrews et al. | |
| 2006/0286154 A1 | 12/2006 | Levy et al. | |
| 2007/0219515 A1 | 9/2007 | Marsh et al. | |
| 2007/0237807 A1 | 10/2007 | Luu | |
| 2007/0265590 A1 | 11/2007 | Sakaguchi | |
| 2007/0292404 A1 | 12/2007 | Walsh et al. | |
| 2007/0292461 A1 | 12/2007 | Tamarkin et al. | |
| 2008/0063694 A1 | 3/2008 | Code | |
| 2008/0142023 A1 | 6/2008 | Schmid et al. | |
| 2008/0147029 A1 | 6/2008 | Pate et al. | |
| 2008/0148994 A1 | 6/2008 | Magnin | |
| 2008/0200890 A1 * | 8/2008 | Wood | A01N 25/10 604/360 |
| 2008/0286320 A1 * | 11/2008 | Vega | A61L 15/50 424/402 |
| 2008/0287535 A1 | 11/2008 | Dekeyser et al. | |
| 2009/0012491 A1 | 1/2009 | D'Addario et al. | |
| 2009/0041820 A1 | 2/2009 | Wu et al. | |
| 2009/0162446 A1 | 6/2009 | Gatto et al. | |
| 2010/0030172 A1 | 2/2010 | Husmark et al. | |
| 2010/0040673 A1 | 2/2010 | Husmark et al. | |
| 2010/0047303 A1 | 2/2010 | Yhlen et al. | |
| 2010/0062031 A1 | 3/2010 | Yoshimasa et al. | |
| 2010/0063466 A1 | 3/2010 | Husmark et al. | |
| 2010/0069861 A1 | 3/2010 | Yao et al. | |
| 2012/0070480 A1 | 3/2012 | Amos | |
| 2013/0165880 A1 | 6/2013 | Amos | |

FOREIGN PATENT DOCUMENTS

| | | |
|---|---|---|
| WO | WO 02/26928 | 4/2002 |
| WO | WO 02/083028 | 10/2002 |
| WO | WO 2005/018530 | 3/2005 |
| WO | WO 2005/051438 | 6/2005 |
| WO | WO 2005/113029 | 12/2005 |
| WO | WO 2007/029198 | 3/2007 |
| WO | WO 2008/057773 | 5/2008 |
| WO | WO 2008/058564 | 5/2008 |
| WO | WO 2009/070630 | 6/2009 |
| WO | WO 2009/148722 | 12/2009 |

OTHER PUBLICATIONS

International Search Report; PCT/US2011/051303; Nov. 16, 2011; 3 pgs.

Polyglykol™ 3350 Product Information. Clariant Corporation (Jan. 2008).

* cited by examiner

ANTIMICROBIAL DISPOSABLE ABSORBENT ARTICLES

CROSS REFERENCE TO RELATED APPLICATIONS

This is a Continuation of application Ser. No. 13/820,155, filed Mar. 1, 2013, which is a national stage filing under 35 U.S.C. 371 of PCT/US2011/51303, filed Sep. 13, 2011, which is a continuation in part of application Ser. No. 12/884,341, filed Sep. 17, 2010, the disclosures of which are incorporated by reference herein in their entirety.

TECHNICAL FIELD

The present disclosure relates to antimicrobial compositions and disposable absorbent articles including coatings of the antimicrobial compositions. These disposable absorbent articles are intended for absorbing body fluids, such as disposable infant diapers, feminine hygiene products including sanitary napkins, panty liners and tampons, products for adult incontinence, personal care wipes, wound dressings, bandages, and household wipes that include a microbial control material.

BACKGROUND

A large variety of disposable absorbent articles are known in the art. These include personal absorbent articles used to absorb bodily fluids such as perspiration, urine, blood, and menses. Such articles also include disposable household wipes used to clean up similar fluids or typical household spills. These disposable absorbent articles are formed from thermoplastic polymers in the form of extruded films, foams, nonwovens or sometimes woven material. An issue with these articles is that they are designed for short term use but may not be disposed of immediately, so that there is an opportunity for microorganisms to grow prior to disposal creating issues with formation of toxins, irritants or odor.

One type of disposable absorbent articles is disposable absorbent garments such as infant diapers or training pants, products for adult incontinence, feminine hygiene products such as sanitary napkins and panty liners and other such products as are well known in the art. The typical disposable absorbent garment of this type is formed as a composite structure including an absorbent assembly disposed between a liquid permeable bodyside liner and a liquid impermeable outer cover. These components can be combined with other materials and features such as elastic materials and containment structures to form a product that is specifically suited to its intended purposes. Feminine hygiene tampons are also well known and generally are constructed of an absorbent assembly and sometimes an outer wrap of a fluid pervious material. Personal care wipes and household wipes are well known and generally include a substrate material, which may be a woven, knitted, or nonwoven material, and often contain functional agents such as cleansing solutions and the like.

An issue with these articles is that once body fluids, or household spills, are absorbed into the articles various microbes can grow in these articles. A well known problem with such articles is the generation of malodors associated with microbial growth and metabolites. For disposable absorbent articles such as infant diapers, products for adult incontinence, and feminine hygiene products, the generation of such malodors can be a source of embarrassment for the user of these products. This can be particularly true for users of adult incontinence and feminine hygiene products. The issue of generation of malodor can include odors that are potentially detectable while the article is being worn and additionally after the article is disposed. In the case of household wipes, the microbes associated generation of malodor is undesirable and can be embarrassing. Additionally the growth of bacteria and other microbes in such household wipes may lead to the undesired spreading of such microbes if the wipe is used subsequent to such microbial growth.

Various odor control solutions include masking, i.e., covering the odor with a perfume, absorbing the odor already present in the bodily fluids and those generated after degradation, or preventing the formation of odors that are associated with microbial growth. Examples of approaches to controlling the generation of malodor by controlling microbial growth include U.S. Pat. No. 6,767,508 (Yahiaui et al.) which teaches the use of nonwoven fabrics that have been treated with an alkyl polyglycoside surfactant solution to result in a heterogeneous system having antibacterial activity when in contact with an aqueous source of bacteria. As discussed in U.S. Pat. No. 6,855,134 (Brooks) the dominant offensive malodors arising from urine biotransformation and urine decomposition are sulfurous compounds and ammonia.

DISCLOSURE OF INVENTION

Figure 1:
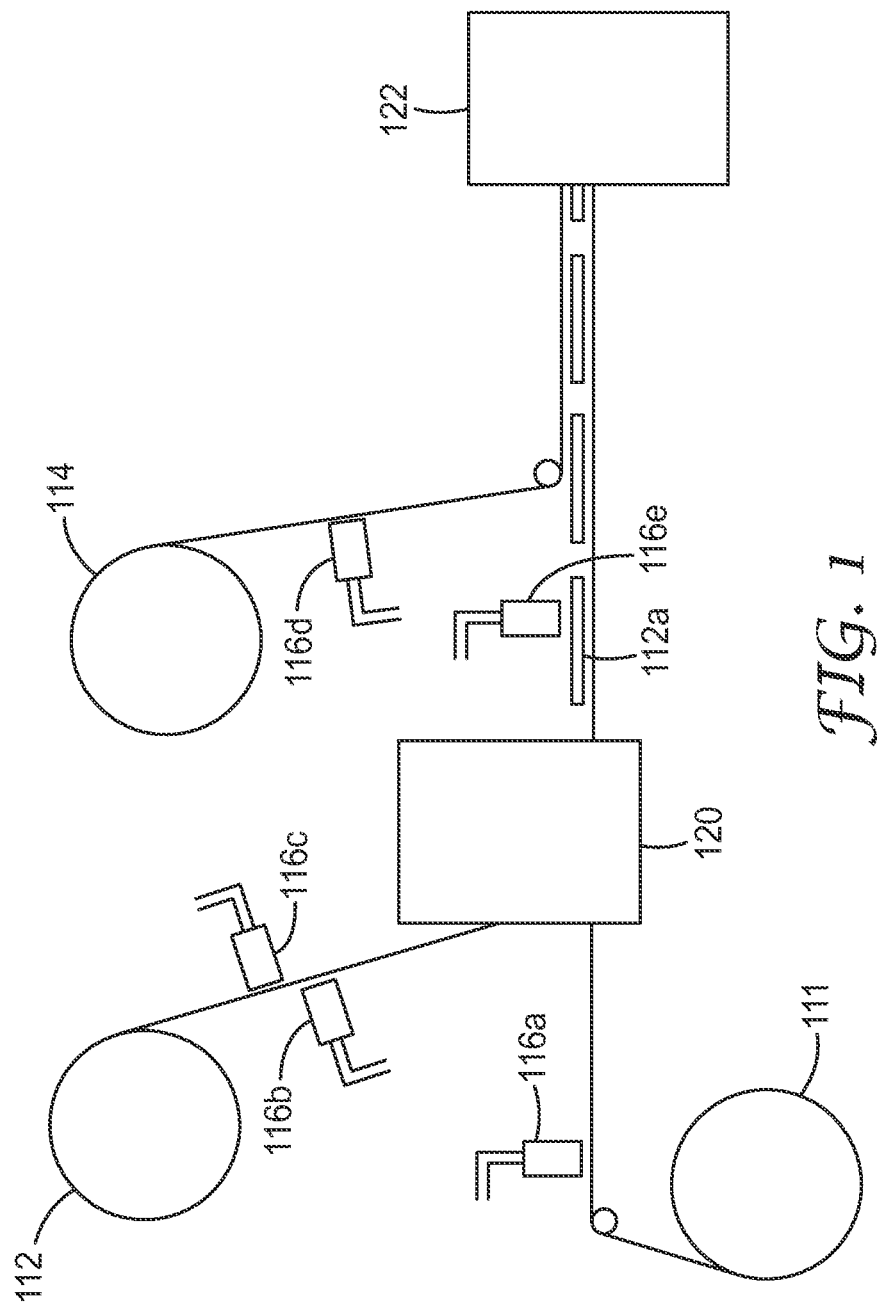
FIG. 1 illustrates a schematic process for making a disposal article having an antimicrobial coating on a surface thereof.

The present disclosure is directed to an antimicrobial composition comprising a carrier comprising fatty alcohol and a poly(alkyleneoxy) polymer, and an antimicrobial agent. Preferably the carrier is hydrophilic to cause aqueous fluids to wet out upon exposure or "insult". The present disclosure is further directed to disposable absorbent articles having a coating of the antimicrobial composition on a surface thereof. In another embodiment, the present disclosure provides a method for preparing such disposable absorbent articles.

As used herein, the term "absorbent article" refers to a device which absorbs and retains body exudates. The term "disposable" is used herein to describe absorbent articles which are not intended to be laundered or otherwise restored or reused as an absorbent article after a single use. Examples of disposable absorbent articles include feminine hygiene articles such as sanitary napkins, panty liners and tampons, diapers, incontinence briefs, diaper holders, training pants, wound dressing, bandages and the like.

The antimicrobial composition may be coated onto one or more layers of the disposable articles, such as by spraying the molten composition. The melt processed antimicrobial component is stable prior to both the manufacture of the final disposable absorbent article and the ultimate end use providing extended antimicrobial activity. Further, when used and exposed to aqueous fluids, the antimicrobial component at least partially dissolves, assisting in releasing the antimicrobial composition or components thereof into the surrounding environment.

Desirably, antimicrobial agents of the antimicrobial composition, when wet, are released into the surrounding medium in which microbes are to be controlled. The antimicrobial agents are released as the carrier dissolves and/or swells when wet, giving the article a self-disinfecting property. The release of the antimicrobial agent may be controlled to adjust the release characteristics of the antimicrobial agent when exposed to moisture. Prior to use the antimicrobial composition is generally dry and is in a generally stable form in or on the absorbent article. The rate of release in water is from 0.1 to 50 mg/minute.

Disposable absorbent articles may be a composite structures that includes an absorbent assembly, such as a fibrous absorbent material, disposed between a liquid permeable bodyside liner and a liquid impermeable outer cover so that the antimicrobial composition may be coated on a nonwoven material or loose fibers that are positioned within the absorbent assembly (e.g. distributed within the bulk of the absorbent), on the body facing side of the absorbent, or on the opposite side of the absorbent assembly. Alternately the antimicrobial composition can be coated on the liquid permeable bodyside liner. Alternately the antimicrobial composition can be coated on a film that can be positioned on the liquid impermeable outer cover side of the absorbent assembly, or on other layers of the disposable absorbent article. Other absorbent materials include foam-based absorbents and super absorbent particles.

When the disposable absorbent article is a tampon, the antimicrobial composition can be coated on a nonwoven material or loose fibers that are positioned within the absorbent assembly or it can be coated on the fluid pervious outer wrap of the tampon.

When the disposable absorbent article is a personal care or household wipe, the substrate of the wipe can incorporate the antimicrobial composition. For example the woven, knitted or nonwoven substrate can be made with a blend of fibers, one of which comprises a coating of the antimicrobial composition. Generally the wipe would be formed from a nonwoven such as by carding or entanglement with a coating of the antimicrobial composition thereon. Alternatively woven or knitted fibers could be provided with a coating of the antimicrobial composition.

Nonwoven webs with a coating of the antimicrobial composition can be prepared via any standard process for directly making nonwoven webs, including spunbond, blown microfiber and nanofiber processes. Additionally fibers or filaments can be prepared and cut to desired lengths and further processed into nonwoven webs using various known web forming processes, such as carding and subsequently coated with the antimicrobial composition. In such cases the chopped fibers may be blended with other fibers in the web forming process. Alternatively fibers or filaments could be woven or knitted alone or in combination with other fibers.

In one embodiment, the disposable absorbent article includes a melt formed thermoplastic polymer substrate and a coating of the antimicrobial composition thereon. Generally, the antimicrobial composition is present at greater than 1 percent by weight relative to the weight of the thermoplastic polymer. The antimicrobial component comprises a carrier, preferably hydrophilic, comprising fatty alcohol and a poly(alkyleneoxy) polymer, and an antimicrobial agent. The thermoplastic polymer substrate may be porous, microporous or non-porous.

Inventive disposable absorbent articles include wound dressing, bandages, disposable diapers, adult incontinent articles or pads, feminine pads, sanitary napkins, catamenial tampons, dental tampons, medical tampons, surgical tampons, nasal tampons or wipes (such as personal cleansing or household wipes) that are preferably dry prior to use but are moist or wet in their end use environment. These disposable absorbent articles are formed using polymeric sheets, natural and polymeric fibers, woven webs, knitted webs, nonwoven webs, porous membranes, polymeric foams, thermal or adhesive laminates, layered compositions, and combinations thereof including a coating of the antimicrobial component as described above.

DETAILED DESCRIPTION OF INVENTION

For the following defined terms, these definitions shall be applied, unless a different definition is given in the claims or elsewhere in the specification.

The term "antimicrobial" or "antimicrobial activity" means having sufficient antimicrobial activity to kill pathogenic and non-pathogenic microorganisms including bacteria, fungi, algae and virus, prevent the growth/reproduction of pathogenic and non-pathogenic microorganisms or control the production of exoproteins.

The term "sufficient amount" or "effective amount" means the amount of the antimicrobial agent when in a composition, as a whole, provides an antimicrobial (including, for example, antiviral, antibacterial, or antifungal) activity that reduces, prevents growth of, or eliminates colony forming units for one or more species of microorganisms.

The term "alkoxy" refers to a group of formula —OR where R is an alkyl group.

The term "alkyl" refers to a monovalent moiety formed by abstraction of a hydrogen atom from an alkane. The alkyl can have a linear structure, branched structure, cyclic structure, or combinations thereof. A cycloalkyl is a cyclic alkyl and is a subset of an alkyl group.

The term "alkylene" refers to a divalent moiety formed by abstraction of two hydrogen atoms from an alkane. The alkylene can have a linear structure, branched structure, cyclic structure, or combinations thereof.

The term "aryl" and "arylene" refers to a mono- or polyvalent moiety of a carbocyclic aromatic compound having one to five connected rings, multiple fused rings, or combinations thereof. In some embodiments, the aryl group has four rings, three rings, two rings, or one ring. For example, the aryl group can be phenyl.

The term "halo" or "halide" refers to chlorine, bromine, fluorine or iodine.

The term "hydrophilic" means the surface has an affinity for water which causes water droplets to spread out over the surface of the article. Generally hydrophilic surfaces have advancing water contact angles of less than 70 degrees.

The term "fatty" means a straight or branched chain alkyl or alkylene moiety having 12 to 22 (odd or even number) carbon atoms, unless otherwise specified. The term "fatty alcohol" refers to a straight or branched chain $C_{12}$ to $C_{22}$ alkanol.

The recitation of numerical ranges by endpoints includes all numbers subsumed within that range.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The carrier of the antimicrobial composition comprises a poly(alkyleneoxy) polymer, which may be mono- or difunctional. The functional groups terminating the poly(alkylene oxide) may include hydroxy groups, amine groups and non-nucleophilic alkoxy or alkylamine groups. Preferably, the poly(alkyleneoxy) polymer, whether a single polymer or a mixture of polymers, has a melting point above 45° C.

Examples of suitable poly(alkylene oxide) polymers include poly(ethylene oxide), poly(propylene oxide), poly (ethylene oxide-propylene oxide)(meth)acrylate, and combinations thereof. Such polymers preferably include nonreactive end groups such as ($C_1$-$C_4$)alkoxy, aryloxy (e.g., phenoxy), and ($C_1$-$C_4$)alkylaryloxy. These groups can be linear or branched.

In some embodiments the poly(alkyleneoxy) polymer component of the carrier comprises a mixture of high and low molecular weight poly(alkyleneoxy) polymers to allow one to adjust the melt viscosity of the carrier. In particular, the poly(alkyleneoxy) polymer component may comprise up to about 50 wt. % (relative to the weight of the carrier) of poly(alkyleneoxy) polymers having molecular weights above 100,000 (Mw). Generally the poly(alkyleneoxy) polymer component may comprise less than 10 wt. % (relative to the weight of the carrier) of the high molecular weight poly(alkyleneoxy) polymers to achieve a desirable melt viscosity. The addition of small amounts of such high molecular weight materials allows one to obtain suitable melt viscosities, 100 to 2000 centipoise, and preferably 500 to 1500 centipoise, at the processing temperatures employed in the coating step.

Suitable poly(alkyleneoxy) polymers include poly(tetramethylene oxide) (available, for example, from Invista, Wichita, Kans., under the trade designation "TERATHANE 2900" (number average molecular weight 2,900 g/mole)), polyethylene glycol (available, for example, from Clariant GmbH Functional Chemicals Division, Frankfurt, Germany, under the trade designation "POLYGLYKOL 35000" (number average molecular weight 35,000 g/mole) "POLYGLYKOL 20000" (number average molecular weight 20,000 g/mole), "POLYGLYKOL 4000S" (number average molecular weight 4000 g/mole), "POLYGLYKOL 8000S" (number average molecular weight 8000 g/mole), "POLYGLYKOL 1500S" (number average molecular weight 1500 g/mole)), CARBOWAX SENTRY (polyethylene glycol, molecular weight 400, diol) from Union Carbide, Danbury, Conn.; PLURONIC L64 (ethylene oxide-propylene oxide-ethylene oxide block copolymer, 2900 molecular weight, liquid diol) from BASF, Gurnee, Ill.; PLURONIC F68 (ethylene oxide-propylene oxide-ethylene oxide block copolymer, 8400 molecular weight, solid diol) from BASF, Gurnee, Ill.; (poly(ethylene glycol-co-propylene glycol), hydroxyl terminal) from Aldrich, Milwaukee, Wis. and CARBOWAX 8000 (polyethylene glycol, molecular weight 8000, solid diol).

In those embodiments, where the hydrophilic carrier will comprise a poly(ethylene oxide) having an average molecular weight in the range from about 100,000 to about 4,000,000, commercial materials include POLYOX WSR N-3000 (number average molecular weight 400,000 g/mole), POLYOX WSR N-750 (number average molecular weight 300,000 g/mole) and POLYOX WSR-301 (number average molecular weight 4,000,000 g/mole), POLYLOX WSR-80 (a polyethylene oxide, 200,000 molecular weight, solid diol) and POLYOX WSRN-10 (a polyethylene oxide, 100,000 molecular weight) from Union Carbide, Danbury, Conn.; POLYLOX WSR-205 (a polyethylene oxide, 600,000 molecular weight, solid diol), POLYOX WSR N12K having an average molecular weight of 1,000,000; POLYOX WSR-301 having an average molecular weight of 4,000,000; POLYOX WSR N60K" having an average molecular weight of 2,000,000; all from Dow Chemical, and UCON 75-H-90,000 (a random ethylene oxide propylene oxide copolymer) from Dow Chemical.

Other poly(ethylene oxide)polymers of a wide range of molecular weights are commercially available from sources such as Sartomer Company, Exton, Pa.; Shinnakamura Chemical Co., Ltd., Tokyo, Japan; Aldrich, Milwaukee, Wis.; and Osaka Organic Chemical Ind., Ltd., Osaka, Japan.

The carrier of the antimicrobial composition further comprises a fatty alcohol. As used herein, a "fatty alcohol" is an alkyl or alkylene mono- or difunctional alcohol, preferably monofunctional, having an even or odd number of carbon atoms. The alcohol may be selected from $C_{12}$-$C_{22}$ saturated fatty alcohols or a ($C_{12}$-$C_{22}$)mono- or poly-unsaturated fatty alcohol. Preferably the fatty alcohol has a melting point of at least 45° C., preferably at least 50° C.

Exemplary fatty alcohols include, but are not limited to, $C_{12}$-$C_{22}$ fatty alcohols such as lauryl alcohol, myristyl alcohol, cetyl alcohol, isostearyl alcohol, isocetyl alcohol, octyl dodecanol, 2-hexyl decanol, and 2-hexyl dodecanol. Preferably, the $C_{12}$-$C_{22}$ fatty alcohol is a solid at ambient conditions, such as the temperatures exposed to during use.

Particularly preferred $C_{12}$-$C_{22}$ fatty alcohols are stearyl alcohol and cetyl alcohol. Cetyl alcohol is safe, non-irritating, and is widely used in pharmaceutical and cosmetics.

The antimicrobial composition further comprises an antimicrobial agent (in addition of the carrier components) to provide the antimicrobial activity especially against Gram-negative bacteria, e.g. *Escherichia coli* and *Pseudomonas* sp. As used herein "antimicrobiobial" refers to testing per American Association of Textile and Color Chemists (AATCC) Test Method 100-2004 (AATCC Technical manual, Vol. 80, 2005, pp. 149-151) and Japanese Industrial Standard (JIS) Z 2801:2000 (Japanese Standards Association, 2001, pp. 1-11). Useful antimicrobial agents are selected to be antimicrobial per either test method, soluble at the application (melt) temperature of the composition in amounts of at least 1 wt. %, and melt-processable at the application temperatures; i.e. does not significantly degrade or react at the application temperatures and a solid at room temperature (23° C.).

For melt processing, preferred antimicrobial components have low volatility and do not decompose appreciably under melt process conditions. The preferred antimicrobial components contain less than 2 wt. % water, and more preferably less than 0.10 wt. % as determined by Karl Fischer analysis.

One or more antimicrobial agents may be used in the antimicrobial compositions at a suitable level to produce the desired antimicrobial activity. Antimicrobial agents are typically present in a total amount greater than 1 wt. %, preferably in an amount greater than 5 wt. %, more preferably in an amount greater than 8 wt. %, relative to the total weight of the antimicrobial composition. In a preferred embodiment, the antimicrobial acid are present in a total amount of no greater than 20 wt. %, or 15 wt-%, based on the total weight of the composition.

The antimicrobial agent may comprise an antimicrobial organic acid, which includes soluble and stable alpha-hydroxy acids, beta-hydroxy acids, other carboxylic acids, including a ($C_2$-$C_6$) saturated or unsaturated alkyl carboxylic acid, a ($C_6$-$C_{16}$) aryl carboxylic acid, a ($C_6$-$C_{16}$) aralkyl carboxylic acid, a ($C_6$-$C_{12}$)alkaryl carboxylic acid, or oligomers that degrade to release one of the above organic acids. Examples of such oligomers are oligomers of glycolic acid, lactic acid or both having at least 4 or 6 repeat units. Various combinations of antimicrobial acids can be used if desired.

The alpha-hydroxy acid, beta-hydroxy acid, and other carboxylic acid antimicrobial acid are preferably present in their protonated, free acid form. It is not necessary for all of the antimicrobial acids to be present in the free acid form; however, the preferred concentrations listed below refer to the amount present in the free acid form. Although less preferred, the conjugate bases, e.g. alkali-, alkali-earth and ammonium salts, may be used provided they provide a homogenous mixture with the carrier. In some embodiments the antimicrobial acids may be substituted with one or more halogen atoms. Additional, non-alpha hydroxy acid, beta-hydroxy acid or other carboxylic acid antimicrobial acids, may be added in order to acidify the formulation or buffer it at a pH to maintain antimicrobial activity. Preferably, acids are used having a pKa greater than about 2.5, preferably greater than about 3, and most preferably greater than about 3.5.

An alpha-hydroxy acid type of antimicrobial acid is typically a compound of the formula:

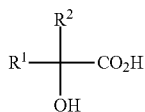

wherein: $R^1$ and $R^2$ are each independently H or a ($C_1$-$C_8$) alkyl group (straight, branched, or cyclic), a ($C_6$-$C_{12}$) aryl, or a ($C_6$-$C_{12}$) aralkyl or alkaryl group (wherein the alkyl group is straight, branched, or cyclic), $R^1$ and $R^2$ may be optionally substituted with one or more carboxylic acid or hydroxy groups.

Exemplary alpha-hydroxy acids include, but are not limited to, lactic acid, malic acid, citric acid, 2-hydroxybutanoic acid, mandelic acid, gluconic acid, glycolic acid, tartaric acid, ascorbic acid, alpha-hydroxyoctanoic acid, and hydroxycaprylic acid, as well as derivatives thereof (e.g., compounds substituted with hydroxyls, phenyl groups, hydroxyphenyl groups, alkyl groups, halogens, as well as combinations thereof). Preferred alpha-hydroxy acids include lactic acid, glycolic acid, malic acid, and mandelic acid. These acids may be in D, L, or DL form and may be present as free acid, salts, or partial salts thereof. All such forms are encompassed by the term "acid." Preferably, the acids are present in the free acid form. Other suitable alpha-hydroxy acids are described in U.S. Pat. No. 5,665,776 (Yu).

A beta-hydroxy antimicrobial acid is typically a compound represented by the formulas:

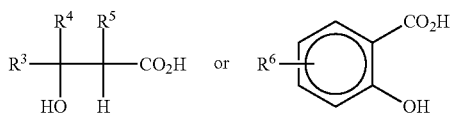

wherein: $R^3$, $R^4$, and $R^5$ are each independently H or a ($C_1$-$C_8$)alkyl group (saturated straight, branched, or cyclic group), ($C_6$-$C_{12}$) aryl, or ($C_6$-$C_{12}$) aralkyl or alkaryl group (wherein the alkyl group is straight, branched, or cyclic), $R^3$ and $R^4$ may be optionally substituted with one or more carboxylic acid groups; and $R^6$ is H, ($C_1$-$C_4$)alkyl or a halogen.

Exemplary beta-hydroxy acids include, but are not limited to, salicylic acid, beta-hydroxybutanoic acid, tropic acid, and trethocanic acid. In certain preferred embodiments, the beta-hydroxy acids useful in the compositions of the present invention are selected from the group consisting of salicylic acid, beta-hydroxybutanoic acid, and mixtures thereof. Other suitable beta-hydroxy acids are described in U.S. Pat. No. 5,665,776.

Carboxylic acids other than alpha- and beta-carboxylic acids are also suitable antimicrobial acids. They include alkyl, aryl, aralkyl, or alkaryl carboxylic acids typically having equal to or less than 12 carbon atoms. A preferred class of these can be represented by the following formula:

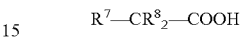

wherein: $R^7$ and $R^8$ are each independently H or a ($C_1$-$C_4$) alkyl group (which can be a straight, branched, or cyclic group), a ($C_6$-$C_{12}$) aryl group, a ($C_6$-$C_{12}$) group containing both aryl groups and alkyl groups (which can be a straight, branched, or cyclic group), $R^7$ and $R^8$ may be optionally further substituted with one or more additional carboxylic acid groups. The carboxylic acid may be a ($C_2$-$C_6$)alkyl carboxylic acid, a ($C_6$-$C_{16}$) aralkyl carboxylic acid, or a ($C_6$-$C_{16}$)alkaryl carboxylic acid. Exemplary acids include, but are not limited adipic acid, sorbic acid, benzoic acid, benzylic acid, and nonylbenzoic acid.

Despite the presence of the antimicrobial acid and fatty alcohol in the antimicrobial compositions, little esterification of the components is observed, even when applied from the melt. It has been observed that less than 1 wt. % of ester is observed after ageing at 40° C. for a day.

Alternatively the antimicrobial agent may comprise cationic amine antimicrobial compounds, which include antimicrobial protonated tertiary amines, biguanidines and small molecule quaternary ammonium compounds.

Exemplary small molecule quaternary ammonium compounds include benzalkonium chloride and alkyl substituted derivatives thereof, di-long chain alkyl ($C_8$-$C_{18}$) quaternary ammonium compounds, cetylpyridinium halides and their derivatives, benzethonium chloride and its alkyl substituted derivatives, octenidine and compatible combinations thereof. Suitable small molecule quaternary ammonium compounds, typically comprise one or more quaternary ammonium group having attached thereto at least one $C_6$-$C_{18}$ linear or branched alkyl or aralkyl chain. Suitable compounds include those disclosed in Lea & Febiger, Chapter 13 in Block, S., *Disinfection, Sterilization and Preservation*, 4$^{th}$ ed., 1991. Exemplary compounds within this class are: chlorohexidine gluconate, monoalkyltrimethylammonium salts, monoalkyldimethyl-benzyl ammonium salts, dialkyldimethyl ammonium salts, benzethonium chloride, alkyl substituted benzethonium halides such as methylbenzethonium chloride and octenidine.

Additional examples of quaternary ammonium antimicrobial agents are: benzalkonium halides having an alkyl chain length of $C_8$-$C_{18}$, preferably $C_{12}$-$C_{16}$, more preferably a mixture of chain lengths, e.g., benzalkonium chloride comprising 40% $C_{12}$ alkyl chains, 50% $C_{14}$ alkyl chains, and 10% $C_{16}$ chains (available as Barquat™ MB-50 from Lonza Group Ltd.); benzalkonium halides substituted with alkyl groups on the phenyl ring (available as Barquat 4250); dimethyldiallylammonium halides having $C_8$-$C_{18}$ alkyl groups, or mixtures of such compounds (available as Bardac 2050, 205M and 2250 from Lonza); and cetylpyridinium halides such as cetylpyridinium chloride (available as Cepacol Chloride from Merrell Labs); benzethonium halides and alkyl substituted benzethonium halides (available as Hyamine™ 1622 and Hyamine 10× from Rohm and Haas). Useful protonated tertiary amines have at least one $C_6$-$C_{18}$ alkyl group.

The antimicrobial agent may comprise a biguanidine, including polybiguanidine, compounds. This class of antimicrobials may be represented by the formula:

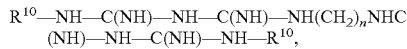
$R^{10}$—NH—C(NH)—NH—C(NH)—NH(CH$_2$)$_n$NHC(NH)—NH—C(NH)—NH—$R^{10}$, where n=3-10, preferably 4-8, and most preferably 6; and $R^{10}$=$C_4$-$C_{18}$ branched or straight chain alkyl optionally substituted in available positions by halogen or $C_6$-$C_{12}$ aryl or alkaryl optionally substituted in available positions by halogen.

Biguanidine compounds are inclusive of polybiguanides. Compounds of this class are represented by the formula:

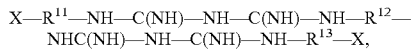
X—$R^{11}$—NH—C(NH)—NH—C(NH)—NH—$R^{12}$—NHC(NH)—NH—C(NH)—NH—$R^{13}$—X, where $R^{11}$, $R^{12}$, and $R^{13}$ are alkylene bridging groups such as polymethylene groups preferably having $C_2$ to $C_{10}$, more preferably $C_4$ to $C_8$ groups and most preferably $C_6$ groups. The alkylene groups can be optionally substituted in available positions with halogen, hydroxyl, or phenyl groups. X is a terminal group and is typically an amine, amine salt, or a dicyandiamide group. An exemplary compound of this class is polyhexamethylene biguanide (PHMB) commercially available as Cosmocil™ CQ from Aveci, Wilmington, Del.

Specific examples of these compounds include, but are not limited to, polyhexamethylene biguanide hydrochloride, p-chlorophenyl biguanide; and A-chlorobenzhydryl biguanide. In another aspect of this embodiment, the biguanide compounds include, but are not limited to, halogenated hexidine such as, but not limited to, chlorhexidine (1,1'-hexamethylene-bis-5-(4-chlorophenyl biguanide) and its salts. One particularly suitable biguanide is polyhexamethylenebiguanide hydrochloride The antimicrobial agent may comprise a phenolic compound having the following general structure:

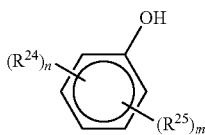

wherein: m is 0 to 3 (especially 1 to 3), n is 1 to 3 (especially 1 to 2), each $R^{24}$ independently is alkyl or alkenyl of up to 12 carbon atoms (especially up to 8 carbon atoms) optionally substituted with 0 in or on the chain (e.g., as a carbonyl group) or OH on the chain, and each $R^{25}$ independently is H or alkyl or alkenyl of up to 8 carbon atoms (especially up to 6 carbon atoms) optionally substituted with 0 in or on the chain (e.g., as a carbonyl group) or OH on the chain, but if $R^{25}$ is H, n preferably is 1 or 2.

Examples of phenolic agent include, but are not limited to, butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, 4,6-di-tert-butyl-resorcinol, methyl paraben (4-hydroxybenzoic acid methyl ester), ethyl paraben, propyl paraben, butyl paraben, 2-phenoxyethanol, as well as combinations thereof. One group of the phenolic compounds is the phenol species having the general structure shown above where $R^{25}$ is H and where $R^{24}$ is alkyl or alkenyl of up to 8 carbon atoms, and n is 0, 1, 2, or 3, especially where at least one $R^{24}$ is butyl and particularly tert-butyl, and especially the non-toxic members thereof being preferred. Some of the phenolic synergists are BHA, BHT, methyl paraben, ethyl paraben, propyl paraben, and butyl paraben as well as combinations of these.

Other additional antimicrobial agents include iodine and its complexed forms such as povidone/iodine, chlorhexidine salts such as chlorhexidine digluconate (CHG), parachlorometaxylenol (PCMX), triclosan, hexachlorophene, surfactants having a $C_{12}$-$C_{22}$ hydrophobe and a quaternary ammonium group, quaternary amines, quaternary silanes, hydrogen peroxide, silver, silver salts such as silver chloride, silver oxide, silver sulfadiazine, and the like.

An optional chelating agent (i.e., chelator) is typically an organic compound capable of multiple coordination sites with a metal ion in solution. Typically these chelating agents are polyanionic compounds and coordinate best with polyvalent metal ions. Exemplary chelating agents include, but are not limited to, ethylene diamine tetraacetic acid (EDTA) and salts thereof (e.g., EDTA(Na)$_2$, EDTA(Na)$_4$, EDTA(Ca), EDTA(K)$_2$), sodium acid pyrophosphate, acidic sodium hexametaphosphate, adipic acid, succinic acid, polyphosphoric acid, sodium acid pyrophosphate, sodium hexametaphosphate, acidified sodium hexametaphosphate, nitrilotris (methylenephosphonic acid), diethylenetriaminepentaacetic acid, 1-hydroxyethylene, 1,1-diphosphonic acid, and diethylenetriaminepenta-(methylenephosphonic acid). Certain carboxylic acids, particularly the alpha-hydroxy acids and beta-hydroxy acids, can also function as chelators, e.g., malic acid and tartaric acid.

Also included as chelators are compounds highly specific for binding ferrous and/or ferric ion such as siderophores, and iron binding proteins. Iron binding protein include, for example, lactoferrin, and transferrin. Siderophores include, for example, enterochelin, enterobactin, vibriobactin, anguibactin, pyochelin, pyoverdin, and aerobactin.

In certain embodiments, the chelating agents useful in the antimicrobial compositions include those selected from the group consisting of ethylenediaminetetraacetic acid and salts thereof, succinic acid, and mixtures thereof. Preferably, either the free acid or the mono- or di-salt form of EDTA is used.

One or more chelating agents may be used in the compositions of the present invention at a suitable level to produce the desired result. They may be used in amounts similar to the antimicrobial agent described above, but are typically used in amounts of less than 5 wt. %.

The ratio of the total concentration of chelating agents to the total concentration of the antimicrobial agent is preferably within a range of 10:1 to 1:100, and more preferably 1:1 to 1:10, on a weight basis.

Compositions of the present invention can optionally include one or more surfactants to promote compatibility of the compositions and to help wet the surface and/or to aid in contacting and controlling or killing microorganisms or preventing toxin production. As used herein the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like. The surfactant can be cationic, anionic, nonionic, or amphoteric. A variety of conventional surfactants may be used; however, it may be important in selecting a surfactant to determine that it is compatible with the finished compositions and does not inhibit the antimicrobial activity of the antimicrobial composition. One skilled in the art can determine compatibility of a surfactant by making the formulation and testing for antimicrobial activity as described in the Examples herein. Combinations of various surfactants can be used. Preferred surfactants are selected from the surfactants based on sulfates, sulfonates, phosphonates, phosphates, poloxamers, alkyl lactates, carboxylates, cationic surfactants, and combinations thereof and more preferably is selected from ($C_8$-$C_{22}$)alkyl sulfate salts, di($C_8$-$C_{18}$)sulfosuccinate salts, $C_8$-$C_{22}$ alkyl sarcosinate, and combinations thereof.

One or more surfactants may be used at a suitable level to produce the desired result. In some embodiments, when used in the composition, they are present in a total amount of between about 0.1 wt. % to about 5 wt-%, based on the total weight of the antimicrobial composition.

For skin contact articles, suitable optional carrier materials include emollients and humectants such as those described in U.S. Pat. No. 5,951,993. In addition, emollients such as oils (for example, hydrocarbons and alkyl esters) and skin acceptable alkyl alcohols and polyethoxylated alcohols, and combinations thereof, also may improve the skin feel of the coated articles. Any indicator that provides a visual change in response to the absence or presence of a specific compound or compounds, such as, water, urea, dissolved oxygen, ions, such as, but not limited to, iron, calcium, magnesium, zinc, sodium, chloride, protons, hydroxide and combinations thereof, sugars, such as, glucose, enzymes, biological materials in the urine and/or feces; and combinations thereof; microbiological flora and fauna, such as, bacteria and the like; some threshold level of a compound or composition, such as, water, urine etc, below a certain amount; and combinations thereof, may be included in the antimicrobial composition. Embodiments of visual indicators include those that change color, color intensity, or change between colorless and colored, or between transparent, translucent and opaque. In particular, color or moisture indicators that provide a color change may be included.

Generally the antimicrobial composition comprises
  a) 80 to 99 wt. %, preferably 90 to 95 wt. % of a carrier, preferably hydrophilic, comprising fatty alcohol and a poly(alkyleneoxy) polymer, wherein the fatty alcohol comprises at least 10 wt. %, preferably at least 20 wt. %, more preferably at least 30 wt. % of the hydrophilic carrier, and the balance being poly(alkyleneoxy) polymer; and
  b) 1 to 20, preferably 5 to 10 wt. % of an antimicrobial agent, preferably an antimicrobial organic acid, based on the total weight of the composition;
  c) 0 to 5 wt. % of surfactant, and
  d) 0 to 5 wt. % other additives as described above.
  such percentages based on the total weight of the antimicrobial composition.

The antimicrobial composition may be prepared by combining the components—the fatty alcohol and the poly(alkyleneoxy) polymer of the carrier components, the antimicrobial agent, and other optional components, and heating to produce a homogenous mixture. In one embodiment, the fatty alcohol and the poly(alkyleneoxy) polymer are combined with the antimicrobial agent at a temperature above that which is necessary to dissolve the antimicrobial agent (at the desired wt %) in the carrier to produce a homogenous mixture. Other optional components may be added to the melt. If any of the components are solids at room temperature (preferably all components are solids at room temperature) this is done at the minimum temperature necessary to melt all components. Exposure of the components to elevated temperatures for extended periods of time should be avoided to retard esterification reactions or heat degradation.

In one preferred embodiment the method involves dissolving the antimicrobial agent component in the carrier component with sufficient heating and mixing to form a homogenous solution; optionally heating the mixture to a temperature sufficient to form a pourable liquid (above its melting point). Desirably, the components are selected to form a homogenous solution when molten, the molten solution may be cooled and solidified, and heated again to form a homogenous solution.

The antimicrobial composition may be applied to component substrates of an absorbent article to produce antimicrobial articles by blending and heating the components of the antimicrobial composition to form a homogenous solution, then coating onto a substrate using a known coating technique such as curtain coating, die coating, knife coating, roll coating, slot coating or spray coating. Preferred coating methods are spray and slot coating of the molten antimicrobial composition. Desirably, the applied molten composition solidifies rapidly on contact with the substrate enabling high production rates. Further, the applied antimicrobial composition does not migrate after coating.

The coating compositions may be applied to one or more surfaces of the components of the disposable absorbent article. The coating composition may be applied to all or a portion of such component substrates, and may be applied as a continuous or discontinuous coating. In some embodiments, the coating compositions may be applied in a preselected pattern. With some substrates, including porous and microporous component of the disposable absorbent article, the coating composition may penetrate the surface and coat a portion of the pores thereof. Useful coating methods are described in Edward Cohen and Edgar Gutoff, "Modern Coating and Drying Technology", VCH Publishers, NY 1992, ISBN 3-527-28246-7.

The antimicrobial composition may be most conveniently applied as essentially solventless liquid or molten compositions. The molten compositions are generally applied to most articles at the lowest temperature required to keep the material suitably molten while maintaining a suitable viscosity. This is typically about 50 to 150° C. The compositions are applied to most non-woven, woven or knitted substrates at a loading of 0.5-50 g/sq meter of the coated area of the coated substrate, more preferably 1-20 g/sq meter, and most preferably at about 2-10 g/sq meter. For melt coating methods, such as spraying the antimicrobial composition, the components are selected so that the composition has a melting point of at least 45° C., preferably at least 50° C. Preferably each of the components have melting points greater than 45° C. Preferably, the antimicrobial composition has a melt viscosity of 100 to 3000 centipoise, preferably 200 to 1000 centipoise, and as measured by the test method described herein at the processing temperatures employed in the coating step—e.g. 50 to 200° C., preferably 50 to 150° C., more preferably 50 to 100° C. Compositions having the desired melt viscosity enable the preferred coating means of spraying the substrate.

Disposable absorbent articles comprising thermoplastic polymer substrates may be made by processes known in the art for making these products using sheets, webs or fibers. These thermoplastic polymers compositions are used to form webs and the like that are directly formed into disposable absorbent articles without special treatments or converting processes. A coating of the antimicrobial composition as applied to the webs or fibers prior to use are dry and in a stable form and remain so until in the end use environment. By dry it is meant that there is no significant water and it is in equilibrium with its environment.

Generally the disposable absorbent articles would be packaged in a dry environment with no added moisture and would not be exposed to moisture until opened and used by the end-use consumer. When in the end-use environment, upon absorption of or exposure to an aqueous fluid, the antimicrobial activity of the composition is expressed and the composition starts or accelerates dissolution and release of the antimicrobial agent. This release continues during use. The composition can be tailored so that the antimicrobial agent will continue to be released after multiple exposures of "insults".

Disposable absorbent articles typically comprise a liquid pervious topsheet, a liquid impervious backsheet and an absorbent core positioned between the topsheet and the backsheet. Disposable absorbent articles and components thereof, including the topsheet, backsheet, absorbent core, and any individual layers of these components, have a body facing surface and a garment facing surface. As used herein "body facing surface" means that surface of the article or component which is intended to be worn toward or adjacent to the body of the wearer, while the "garment facing surface" is on the opposite side and is intended to be worn toward or placed adjacent to the wearer's clothing or undergarments when the disposable absorbent article is worn.

The following description generally discusses the absorbent core, topsheet, and backsheet materials that are useful in disposable absorbent articles. It is to be understood that this general description applies to these components of the specific absorbent articles shown in the Figures and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). In addition to absorbent composites, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue, including tissue wraps and tissue laminates; absorbent foams; absorbent sponges; superabsorbent polymers; absorbent gelling materials; or any equivalent material or combinations of materials, or mixtures of these.

The configuration and construction of the absorbent core may be varied (e.g., the absorbent core may have varying caliper zones and/or have a profile so as to be thicker in the center; hydrophilic gradients; gradients of absorbent composites; superabsorbent gradients; or lower average density and lower average basis weight zones, e.g., acquisition zones; or may comprise one or more layers or structures). The total absorbent capacity of the absorbent core should however, be compatible with the design loading and the intended use of the absorbent article. Further, the size and absorbent capacity of the absorbent core may be varied to accommodate different uses such as diapers, incontinence pads, panty liners, regular sanitary napkins, and overnight sanitary napkins, and to accommodate wearers ranging from infants to adults. The absorbent core can also include other absorbent components that are often used in absorbent articles, for example, a wicking, distribution or acquisition layer, or a secondary topsheet for increasing the wearer's comfort.

The topsheet is preferably compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), including apertured nonwovens; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, spunlace carded, wet-laid, melt-blown, hydroentangled, hydroformed, hydroapertured, combinations of the above, or the like. Whether comprised of a woven or nonwoven material, the topsheet preferably comprises skin care compositions comprising proton donating active(s), as described further below.

The backsheet is impervious to liquids (e.g., menses and/or urine) and preferably comprises a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm. (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished providing a more clothlike appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

The backsheet and the topsheet are positioned adjacent the garment facing surface and the body facing surface, respectively, of the absorbent core. The absorbent core is preferably joined with the topsheet, the backsheet, or both in any manner as is known by attachment means such as those well known in the art. However, embodiments of the absorbent articles are envisioned wherein portions or the entire absorbent core are unattached to either the topsheet, the backsheet, or both.

For example, the backsheet and/or the topsheet may be secured to the absorbent core or to each other by a uniform continuous layer of adhesive, a patterned layer of adhesive, or a patterned array of adhesive. Adhesives which have been found to be satisfactory are manufactured by H.B. Fuller Company of St. Paul, Minn. under the designation HL-1258 or H-2031. The attachment means will preferably comprise an open pattern network of filaments of adhesive as is disclosed in U.S. Pat. No. 4,573,986, (Minetola, et al.) and which is incorporated herein by reference. An exemplary attachment means of an open pattern network of filaments comprises several lines of adhesive filaments swirled into a spiral pattern as illustrated by the apparatus and method shown in U.S. Pat. No. 3,911,173 (Sprague, Jr.); U.S. Pat. No. 4,785,996, (Zwieker, et al.); and U.S. Pat. No. 4,842,666, (Werenicz). Each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

Reference may be made to U.S. 2002/0147433 (McOskar et al.), incorporated herein by reference, for further details regarding the construction of disposable absorbent articles.

Optionally, the disposable absorbent article may further comprise a liquid distribution layers (also known as an acquisition distribution layer) for improving the liquid distribution and absorption properties of the absorbent articles.

Numerous approaches have been suggested and include the use of channels, reservoirs, apertures, etc., that have been introduced generally into the absorbent core and occasionally into a wicking layer by methods such as embossing, corrugation, cutting or folding. See, for example, U.S. Pat. No. 4,676,786 (Nishino), U.S. Pat. No. 4,678,464 (Holtman), U.S. Pat. No. 4,655,759 (Romans-Hess et al.), U.S. Pat. No. 5,030,229 (Yang), U.S. Pat. No. 3,769,978 (DeNight et al.), U.S. Pat. No. 4,758,240 (Glassman), U.S. Pat. No. 4,795,453 (Wolfe), U.K. Patent No. 2,017,505 (Fitzgerald) and WO 86/01378 (Kamstrup-Larson). In WO 91/11161 there is proposed corrugation of the nonwoven liquid permeable topsheet of an absorbent product. U.S. Pat. No. 4,735,624 (Mazars) discloses a disposable diaper comprising an absorbent pad constituted by an absorbent material consisting essentially of hydrophilic fibers joined to one another to form a coherent mass. The pad is narrow in the crotch area and widens out in the front and rear areas of the diaper with branches.

The use of a plastic netting material to promote the unidirectional spreading of liquids in absorbent pads is disclosed in European Patent No. 0 174 152 B1. The use of certain complex shaped fibers, in tow or staple form, that are capable of transporting liquid in absorbent articles are disclosed in European Patent Application (E.P.A.) No. 0 391 814 A2 (Phillips et al.) and WO 91/12949 (Thompson) (who discloses fibers or sheets with an extremely large ratio of surface area to mass), and E.P.A. No. 493 728 A1 which discloses a notched fiber with notch angles (cc) less than (180'-), where 0 is the liquid fiber contact angle. U.S. Pat. No. 4,798,604 (Carter) discloses a contoured polymeric film which is apertured and contains a pattern of raised areas that may be employed to form the body contacting surface, i.e., topsheet, in absorbent devices. Films have also been proposed as liquid distribution layers in absorbent articles in WO 95/00093 where a liquid distribution strip is used in association with an absorbent strip. The liquid distribution strip is shorter and wider than the absorbent strip. The two strips are located between the topsheet and the absorbent core of the absorbent article (e.g., a sanitary napkin) The liquid distribution strip can be a polyethylene film which can be apertured and in one alternative embodiment has troughs. In French Patent No. 2,082,526 a diaper or tampon is provided with a drain that is a pleated sheet of nonwoven placed in the absorbent pad.

U.S. Pat. No. 5,728,446 (Johnston et al.) discloses a liquid management film comprising a thermoplastic film having at least one microstructured hydrophilic surface with a plurality of primary grooves. The primary grooves have at least two secondary grooves, each of said secondary grooves forming at least one notch which notches are substantially parallel and separated by a secondary peak. U.S. Pat. No. 5,514,120 (Johnston et al.) describes an absorbent article comprising an optional liquid permeable topsheet, an optional backsheet, an absorbent core disposed between the topsheet and backsheet and at least one liquid management member which comprises a film having at least one microstructure-bearing hydrophilic surface that promotes rapid directional spreading of liquids, the liquid management member and core being in contact. U.S. Pat. No. 4,824,718 (Hwang) describes a disposable article such as a diaper or feminine hygiene product having a rattle-free, liquid impermeable, vapor permeable, microporous, polymeric film having pores defining passages extending therethrough, the passages being partially filled with a rattle-reducing additive material and a method for making same is disclosed.

Each of the aforementioned references incorporated herein by reference. These and other liquid distribution films are known in the art of disposable absorbent products, and may be incorporated into the articles disclosed herein.

The inventive absorbent articles have also been found to significantly reduce unpleasant odors and as such are useful in wipes or disposable absorbent garments where there is often odor generated, such as by conversion of urea to ammonia by *Proteus mirabilis*. The antimicrobial articles can be used to reduce microbial activity on the skin when in contact for extended periods of time. The absorbent articles can be used as an absorbent fibrous material or as additive fibers in an absorbent material or as a cover web or film adjacent an absorbent material, or as a cover web that is in contact with the skin. These uses include a topsheet for a diaper, a bed pad or a feminine pad. In these uses the antimicrobial articles could be formed from a spunbond web or like nonwoven and used in a body contacting environment. In this case the loading levels should be sufficient to kill or inhibit bacterial growth over an extended period of time. The antimicrobial articles when used as, in or adjacent an absorbent core can have relative high loading levels of the antimicrobial compositions to kill microbes to inhibit odor production.

The level of antimicrobial activity in a given use environment is related to the finished composition, including the weight percents of the antimicrobial agent, as well as the presence and weight percent of additional components such as surfactants and wetting agents. The rate of release of the antimicrobial agent is largely controlled by the relative amounts of fatty alcohol and a poly(alkyleneoxy) polymer in the carrier, as well as the concentration of the antimicrobial agent, solubility in the carrier and use temperature. Increasing the amount of fatty alcohol in the carrier and can retard the release of the antimicrobial agent to provide extended antimicrobial activity. Decreasing the amount of fatty alcohol in the carrier enables the enhanced rate of release of antimicrobial agent. The rate of release may be controlled or designed based on the intended end-use of the disposable absorbent article The level of antimicrobial activity is also related to the amount of the antimicrobial composition and antimicrobial agent that is present in the disposable absorbent articles as well as where and how the material is incorporated into the disposable article. An additional aspect potentially impacting the level of antimicrobial activity is the total surface area of the coated component substrate within the disposable absorbent article. Thus one way to increase the antimicrobial activity at a given weight within a disposable absorbent article is to coat nonwovens or fibrous substrates and thus more surface area per unit weight.

The rate of release of antimicrobial agents from the antimicrobial composition may be affected by incorporation of plasticizers, surfactants, enhancers, humectants, wetting agents as well as other components. Suitable humectants and/or wetting agents may include polyhydric alcohols such as low molecular weight polypropylene glycol and polyethylene glycol.

In a preferred embodiment the articles of the present invention are kept dry until use. This protects the antimicrobial composition that may be present from dissolution of the carrier. The amount of moisture present is preferably low. Typically, the amount of water in the packaged article prior to use is less than 10% by weight, preferably less than 8% by weight and usually less than 5% by weight. Packaging may be used that protects the article from absorbing moisture in humid environments. For example, the articles may be packaged with a protective film of polyolefin, polyester (e.g. polyethylene terephthalate, polyethylene naphthylate etc.), flouropolymers (e.g. Aclar available from Allied Signal Morristown, Pa.), PVDC, PVC, ceramic barrier coated films, as well as laminates and blends thereof.

Generally, automated equipment can be used similar to conventional production lines for sanitary napkins, adult incontinence pads, diapers, and the like, with minor modifications to produce the disposable absorbent articles. Modular systems are especially preferred, wherein the various unit operations in the production line can be moved and replaced with other modules without necessitating a complete rebuild of the production machine.

The production line can include a hammermill for production of comminuted fibers, if fluff pulp is to be used, or absorbent material in roll form can be provided, including airlaid webs, mechanically softened pulp sheets, tissue webs, and the like. Likewise the nonwovens or film components, such as a nonwoven top sheet and a film backsheet, of the absorbent article are also generally provided in roll form. Roll goods are unwound and cut to shape, using methods such as die cutting, slitters, or water jets, and the components placed in proper relationship one to another, typically with online bonding at selected regions provided by spray adhesive, contact with ultrasonic horns or heated embossing elements, or other bonding means known in the art. Components may be moved on continuous belts from one operation to another.

For example, a web of nonwoven that serves as the topsheet of the absorbent article can be provided in a roll form, unwound and directed in a continuous fashion in the machine direction of the production line. Simultaneously a web of an absorbent material, such as an airlaid, can be provided in a roll form, unwound and directed in a continuous fashion in the machine direction of the production line into a unit operation that cuts discrete pieces of this web and places the discrete pieces onto the continuous top sheet in a spaced apart, in the machine direction, manner to serve as the absorbent core of the finished absorbent article. Likewise a fluid impervious web, e.g. a film, breathable film, or a laminate of such a film and a nonwoven web, may be provided in a roll form, unwound and directed in the machine direction of the production line, and placed in continuous fashion on top of the discrete pieces of absorbent material and topsheet material to sandwich the absorbent between the topsheet and the fluid impervious backsheet materials. These components can be attached to each other using known methods, such as adhesive bonding, sonic bonding, bonding with heat and or pressure, or other suitable means to yield a composite running length that is then cut into individual absorbent articles for packaging.

FIG. 1 shows a basic process schematic for producing the disposable absorbent articles of the invention. In FIG. 1 a roll of backsheet 111 is provided, unwound, and directed in the machine direction of the production machine, a roll of an absorbent web 112 is provided, unwound, and directed in the machine direction the production machine and into a unit operation 120 that cuts the absorbent web into discrete pieces 112a and places them and attaches them onto the backsheet in a spaced apart configuration.

Also shown in FIG. 1 is a roll of topsheet 114, which is unwound, and directed in the machine direction of the production machine and is attached to the absorbent material and the backsheet. The means for attaching these components is not shown in FIG. 1, but can include adhesive bonding, sonic bonding, bonding by heat and or pressure, and other known bonding methods, or a combination of such methods.

Shown in FIG. 1 are alternate envisioned placements of the applicator 116a through 116e, for providing the antimicrobial coating onto the desired component of the disposable absorbent article. Thus the applicator 116a is positioned to apply the antimicrobial coating onto the body facing surface of the backsheet material unwinding off of the roll of backsheet material 111. Depending on the exact type of application used, this coating can be in the form of stripes or a continuous or discontinuous layer. For example if stripes are desired, a slot type applicator, as well known in the art, can be used. Alternately if a spray type applicator is used, also well known in the art, the coating can be in the form of a continuous or discontinuous coating, depending on the specific applicator settings and the application weight. In both cases, slot type applicator and spray type applicator, the coating can be provided in a discontinuous manner in the machine direction for each of the embodiments shown in FIG. 3A through FIG. 3F.

In FIG. 1 the applicator 116b is shown positioned to apply the antimicrobial coating to the garment facing surface of the absorbent web as it is unwound from the roll of absorbent material 112. The applicator 116c is positioned to apply the antimicrobial coating to the body facing surface of the absorbent material as it is unwound from the roll of absorbent material 112. The applicator 116d is shown positioned to apply the antimicrobial coating to the garment facing surface of the topsheet as is unwound form a roll of topsheet material 114. The applicator 116e is shown positioned to apply the antimicrobial coating to the body facing side of the discrete pieces of the absorbent web 112a. The placement of the antimicrobial coating within the disposable absorbent article of the invention can be determined by selecting among various locations of the applicators 116a through 116e for the antimicrobial coating illustrated in FIG. 1. It is also envisioned that it may be desired to apply the antimicrobial coating onto more than one location within the disposable absorbent article, which can be achieved by utilizing more than one applicator and one applicator location. In FIG. 1 the final step of producing the disposable absorbent articles involves cutting individual articles from the combined web and packaging these articles in unit operations show as 122.

Figure 2:
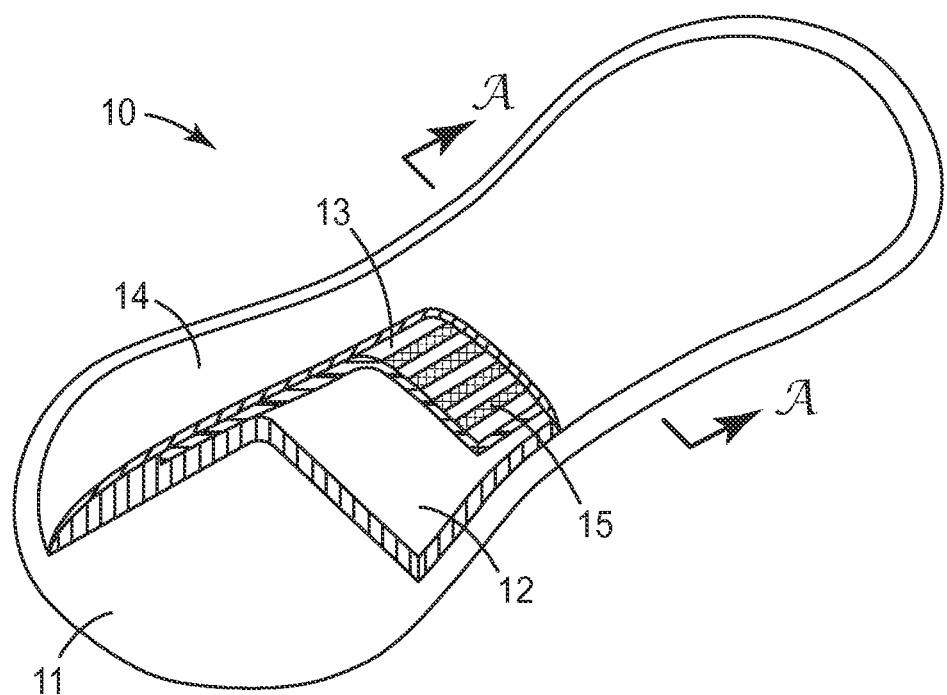
FIG. 2 shows a cutaway of a disposable article in the form of a pad having an antimicrobial coating.

FIG. 2 shows an exemplary disposable article 10 in cut-away with a backsheet 11, topsheet 14, a, an absorbent core 12, and an acquisition distribution layer 13, wherein the antimicrobial coating 15 is shown as a coating having a predetermined pattern on the absorbent core 12.

The cross section view of various embodiments of the coating on disposable articles are shown in FIG. 3A through FIG. 3F. The difference in the embodiments shown in FIG. 3A through FIG. 3F are with the placement of the antimicrobial coating within the article. In the FIG. 3A through FIG. 3F the disposable absorbent article 10, in the form of a pad, comprises a topsheet 14, a backsheet 11, an absorbent core 12, and an acquisition distribution layer 13, wherein the antimicrobial coating 15 is shown on various component surfaces of the article.

Figure 3A:
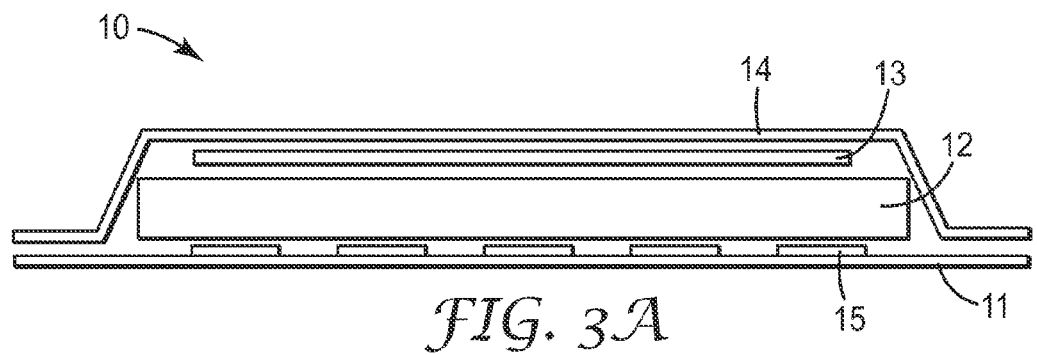
FIG. 3A-3F illustrates alternate embodiments in cross section of disposable articles having an antimicrobial coating.

FIG. 3A shows an exemplary disposable article in cross section, e.g. through line AA of FIG. 2, wherein the antimicrobial coating 15 is in the form of a pattern (such as the illustrated stripes) coated onto the body facing surface of backsheet 11.

Figure 3B:
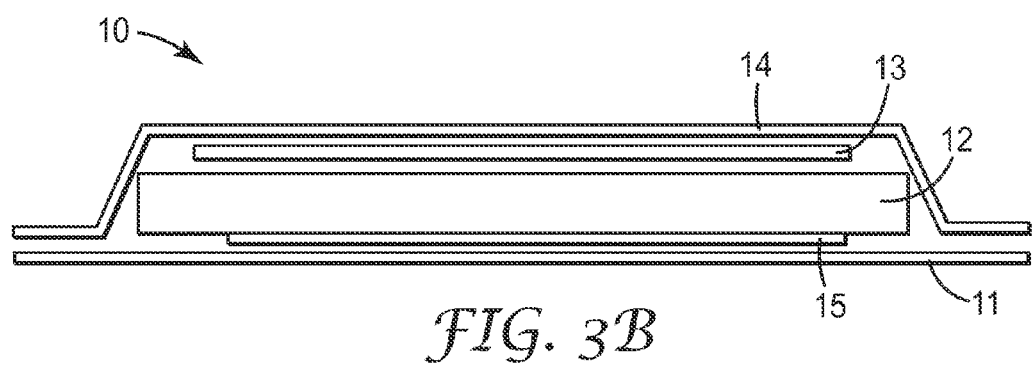

FIG. 3B shows an alternate exemplary disposable absorbent article of the invention in cross section wherein the antimicrobial coating 15 is in the form of a layer coated onto the garment facing surface of the absorbent core 12. Such a layer can be continuous (as shown) or comprise a discontinuous coating as may be achieved by a spray coating application.

Figure 3C:
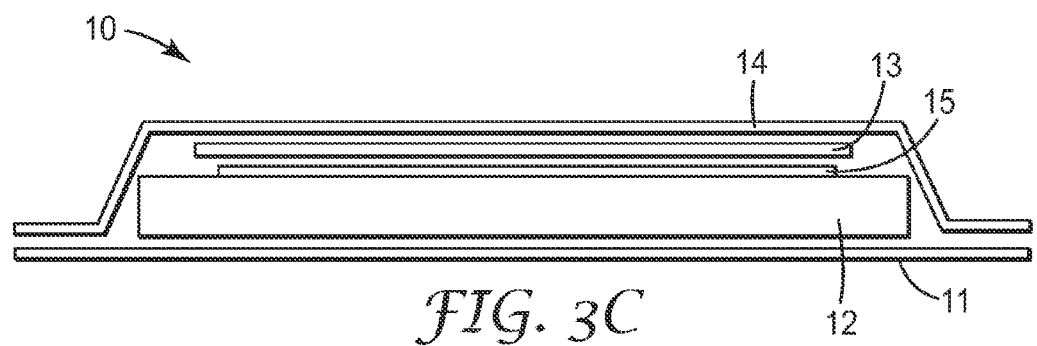

FIG. 3C shows an alternate exemplary disposable absorbent article of the invention in cross-section wherein the antimicrobial coating 15 is carried on the body facing surface of the absorbent core 12, and wherein the antimicrobial coating is a continuous (as shown) or discontinuous layer on the body facing surface of the absorbent core 12.

Figure 3D:
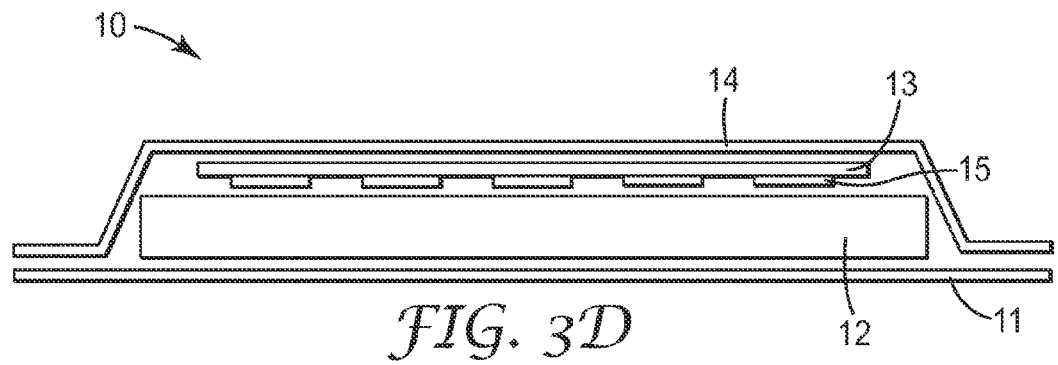

FIG. 3D shows an alternate exemplary disposable absorbent article of the invention in cross-section wherein the antimicrobial coating 15 is carried on the garment facing surface of the acquisition distribution layer 13, and wherein the antimicrobial coating 15 is in the form of a pattern (such as the illustrated stripes).

Figure 3E:
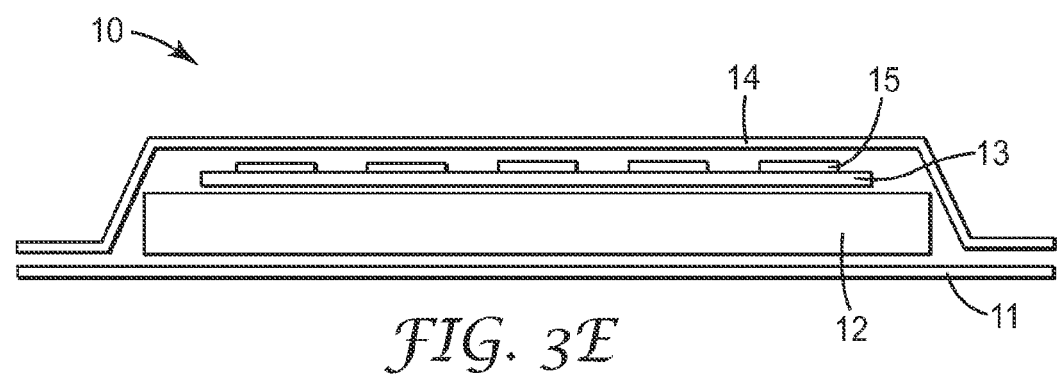

FIG. 3E shows an alternate exemplary disposable absorbent article of the invention in cross-section wherein the antimicrobial coating 15 is placed on the body facing surface of the acquisition distribution layer 13, and wherein the antimicrobial coating 15 is in the form of a pattern (such as the illustrated stripes).

Figure 3F:
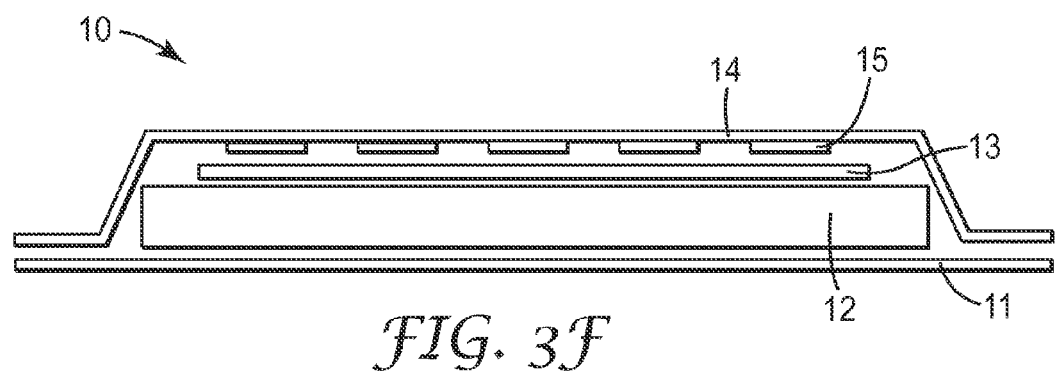

FIG. 3F shows an alternate exemplary disposable absorbent article of the invention in cross-section wherein the antimicrobial coating 15 is carried on the garment facing surface of topsheet 14 and wherein the antimicrobial coating is in the form of a pattern (such as the illustrated stripes).

With regard to each of the depicted embodiments the antimicrobial coating is shown as a discreet layer. The layer may be patterned or non-patterned and may coat all or a portion of the selected component of the disposable absorbent article. One of more components may be coated. For component substrates that are porous or microporous, it will be understood that the antimicrobial composition may fully or partially penetrate the voids thereof.

The disposable article may further comprise a visual indicator, which may be integral to one or more components of the article, or may be a separate article bonded or otherwise affixed to one or more components of the article, including a surface of the topsheet, backsheet, absorbent material or other constituent components of a disposable article. In some embodiments, the visual indicator is a component of the antimicrobial composition, that may be coated on one or more surfaces of the article.

As previously described, any indicator that provides a visual change in response to the absence or presence of a specific compound or compounds, such as, water, urea, dissolved oxygen, ions, such as, but not limited to, iron, calcium, magnesium, zinc, sodium, chloride, protons, hydroxide and combinations thereof, sugars, such as, glucose, enzymes, biological materials in the urine and/or feces; and combinations thereof; microbiological flora and fauna, such as, bacteria and the like; some threshold level of a compound or composition, such as, water, urine etc.; and combinations thereof, may be included in the visual indicator component of the disposable article. Embodiments of visual indicators include those that change color, color intensity, or change between colorless and colored, or between transparent, translucent and opaque. In particular, color or moisture indicators that provide a color change may be included.

A number of differing compositions or methods of construction have been suggested for indicating that a diaper is wet. For instance, U.S. Pat. No. 4,231,370 to Mroz et al. discloses a pH change/color change wetness indicator which is a solid mixture dispersed in an adhesive. U.S. Pat. No. 4,022,211 to Timmons et al. discloses a water soluble coloring agent which is visible when the diaper is dry, but which disappears when the diaper becomes wet. U.S. Pat. No. 3,952,746 to Summers discloses the use of humidity indicator paper mounted on an absorbent area of the diaper. U.S. Pat. No. 4,327,731 to Powell discloses moisture activated enzymatic systems and chromogens or pigment producing agents used as wetness detectors. U.S. Pat. No. 3,759,261 to Wang and U.S. Pat. No. 4,192,311 to Felfoldi disclose masked color layers which become visible when intervening layers become wet. U.S. Pat. No. 4,931,051 (Castello) describes a wetness indicator comprising a hydratable salt mixture applied to a water permeable membrane and visible from an external observation of the absorbent pad. U.S. 20100262100 (Klofta) describes a wetness indicator composition comprising a stabilizer, a colorant, and a matrix. U.S. 2009/0326494 (Uchida et al.) describes an absorbent article having applied thereon a hot-melt wetness indicator composition that changes color on contact with a body fluid comprising (a) a pH indicator that is substantially colorless at pH 7 and develops a color in an acidic environment, (b) a surfactant, (c) a polyalkylene glycol, (d) a polymer having a carboxyl group, and (e) an acidic substance other than components (b) and (d).

The invention will be further clarified by the following examples which are exemplary and not intended to limit the scope of the invention.

EXAMPLES

Test Methods

Odor Testing in Artificial Urine

To create the test inoculum, an overnight culture of *Proteus mirabilis* ATCC #14153 grown in tryptic soy at 37° C. was diluted 1:50,000 into filter-sterilized artificial urine (prepared according to Sarangapani et al., J. Biomedical Mat. Research 29:1185) containing 5% (v/v) tryptic soy broth (TSB, from Becton, Dickinson and Company, Franklin Lakes, N.J.). Test materials were placed into sterilized 100 mL Pyrex bottle and inoculated such that the test material was not saturated by the inoculum. Unless otherwise noted, 3 mL of inoculum was added to a 1-inch diameter core cut from a personal hygiene article. The bottles were sealed and incubated for approximately 24 hours at 37° C. After incubation, one to four people were asked to briefly open the jars under their noses and rate the samples for ammonia odor. Ammonia test strips (pHydrion) were used to estimate the ammonia concentration (in ppm) for samples as indicated.

Odor Testing in Artificial Menses

To create the test inoculum, an overnight culture of *Pseudomonas aeruginosa* ATCC #9027 was diluted 1:50,000 into 40% (v/v) sheep's blood (defibrinated, from PML Microbiologicals) in Brain Heart Infusion broth (BHI, from Becton, Dickinson and Company, Franklin Lakes, N.J.). Test materials were placed into sterilized 100 mL Pyrex bottle and inoculated such that the test material was not saturated by the inoculum. Unless otherwise noted, 3 mL of inoculum was added to a 1-inch diameter core cut from a personal hygiene article. The bottles were sealed and incubated for approximately 24 hours at 37° C. After incubation, one to four people were asked to briefly open the jars under their noses and rate the samples for malodor.

Antimicrobial Activity Testing

Antibacterial activity of samples was evaluated using Japanese Industrial Standard (JIS) L 1902 with the following modifications:
- Sample size was not 0.4 g as indicated in JIS L 1902. Sample size for each test material was noted and was chosen such that sample was nearly completely wetted by the addition of 0.2 mL inoculum.
- Samples were not sterilized prior to evaluation using JIS L 1902.
- D/E neutralizing broth (from Becton, Dickinson, and Company, Franklin Lakes, N.J.) was used in place of physiological saline for shake-out
- Aerobic count PETRIFILM (from 3M, St. Paul, Minn.) was used in place of Nutrient B agar for plating of bacteria.

To quantify antibacterial activity, the growth value (F) and bacteriostatic activity value (S) were calculated as described in JIS L 1902.

Viscosity Test

Viscosity measurements were obtained using a Stress/Strain rheometer, model AR2000 manufactured by TA Instruments, New Castle, Del. The fixture was a set of 40 mm parallel plates with the lower plate being temperature controlled using a peltier heater. The test sample (approximately 1.9 grams) was set on the lower plate and the top plate was lowered so that there was a gap of 1.5 mm between the plates. The sample was initially melted and equilibrated at 90° C. and then lowered to 50° C. to begin the analysis. Starting at a temperature of 50° C., a small amplitude oscillatory deformation was performed under the following conditions: frequency of 1 Hz, strain amplitude of 1%, and temperature sweep of 50-100° C. in increments of 10° C. Data collected and reported was the complex viscosity, Eta* in centipoise as a function of temperature, ° C.

Materials

Salicylic acid (SA), available from Mallinckrodt, Philipsburg, N.J.

PEG 3350, polyethylene glycol, available from Dow Chemical, Baton, Wash.

Cetyl Alcohol (CA), available from Proctor & Gamble, New Mitford, Conn.

Cis-13-Docosenol, available from Tokyo Chemical Industry America, Portland, Oreg.

1-Eicosanol, available from Tokyo Chemical Industry America, Portland, Oreg.

Citric acid, available from Alfa Aesar, Ward Hill, Mass.

Adipic acid, available from Spectrum Chemicals, Gardena, Calif.

5-Chlorosalicylic Acid, available from Alfa Aesar, Ward Hill, Mass.

Sample Preparation

Preparation of Melt Processable Antimicrobial Compositions

Antimicrobial compositions were prepared using the components shown in the Tables. The individual components were weighed and added to an appropriately sized test tube (batch size was approximately 1 gram). The test tube was heated by partially immersing it in an oil bath at a temperature of 90° C. All of the compositions were homogeneous in the molten state at this temperature.

Preparation of Antimicrobial Coated Nonwoven Substrates

Hand Coated

Small samples of nonwoven substrates were hand coated with the antimicrobial compositions for testing using the following procedure. The coating method involved coating the molten compositions onto aluminum foil that was wrapped around a 4 inch by 8 inch glass plate seated on a hot plate. The hot plate was set to provide a surface temperature on the aluminum foil of about 75° C. to keep the coated composition molten on the foil. The coating on the aluminum foil was done in an area larger than the test piece of substrate. This coating was done using a small paint brush. The nonwoven substrate (a 4 inch by 6 inch piece of Wypall L30 tissue, available from Kimberly-Clark Corporation, Roswell, Ga.) was then placed onto the coated molten composition on the aluminum foil and pressed lightly by hand, for a few seconds, against the coated aluminum foil to transfer some of the composition to the substrate. The substrate piece was then removed from the foil and allowed to cool. By comparing the tare weight of the substrate piece to the coated weight, the weight of antimicrobial composition transferred to the substrate in this procedure was determined.

Spray Applicator

Additional samples were prepared by coating the compositions using a spray applicator. These samples were prepared by placing several kilograms of the composition to be applied into a tank type melter (S series melter, model number S5N2ZES1-FMG-V5.32S, available from Illinois Tool Works, Inc., Glenview, Ill.) which was set to a temperature of 70° C. Once the composition had completely melted it was pumped thru a heated hose to a spray head (Model UA 6UM R8D06, S/N: DV05003311, available from Nordson Corporation, Westlake, Ohio) which was set at a die temperature of 70° C. and an air temperature of 70° C. to produce a spray of the molten composition which was directed downward onto a nonwoven substrate (hard roll paper towel, available from Kimberly-Clark Corporation, Roswell, Ga.) moving continuously beneath the nozzle. The distance between the tip of the nozzle and the substrate was 3 inches. The lineal speed of the nonwoven substrate web was adjusted to achieve a coating weight of approximately 50 grams/meter$^2$ (gsm). To prepare sufficient material for such coating trials, 7.5 kg batches of some compositions were prepared by charging the components into a 10 liter glass vessel and heating and mechanically stirring until the molten composition appeared homogeneous (approximately 25 minutes). The molten composition was then poured into aluminum pans, to a thickness of about 5 mm and allowed to cool to solidify. Once solidified the material was broken up into pieces between 1 cm$^2$ and about 3 cm$^2$ in the XY direction of the solidified slabs in the aluminum pans.

Pad Preparation

To determine the ability of the antimicrobial compositions to inhibit odor in absorbent articles such as feminine hygiene pads, disposable infant diapers, and absorbent articles for adult incontinence, pad samples were prepared as follows. Nonwoven substrates were coated with antimicrobial compositions of the present invention as described above. A commercially available feminine hygiene pad (Always Maxi, available from Procter & Gamble Co, Cincinnati, Ohio) was obtained and a 1 inch (2.54 cm) diameter circular piece of the article was stamped out of the pad. 1 inch (2.54 cm) diameter circular pieces were also stamped out of the coated nonwoven substrates prepared as described above. Two circular pieces of coated nonwoven substrate were then inserted into the circular pieces of the feminine hygiene pad for odor testing, as described above. For each example tested a piece of the coated nonwoven substrate was placed approximately at the top (i.e., below the topsheet) and approximately at the bottom (i.e., above the backsheet) of the stamped out pad.

Control Examples 1-3 and Examples 1a-14

Pad samples were prepared and artificial urine odor testing was carried out as described above. For these examples, the antimicrobial composition was hand coated onto the nonwoven substrate. The amount of SA ranged from 4 weight percent to 20 weight percent and the PEG 3350:CA carrier ratio was either 2:1 or 1:1. Several samples of unmodified pads were also tested as controls. The antimicrobial coating compositions and odor testing results are shown in Table 1.

TABLE 1

| Example | SA (weight %) | PEG 3350:CA ratio | Pad weight (grams) | Antimicrobial coating weight (grams) | Odor testing-artificial urine |
|---|---|---|---|---|---|
| Control 1 | none | none | not recorded | 0.0000 | strong odor (50 ppm) |
| Control 2 | none | none | 0.42 | 0.0000 | strong odor (50 ppm) |
| Control 3 | none | none | 0.37 | 0.0000 | strong odor (50 ppm) |
| 1a | 4% | 2:1 | 0.37 | 0.1130 | no detectable odor (0-5 ppm) |
| 1b | 4% | 2:1 | 0.41 | 0.1162 | some detectable odor (20-50 ppm) |
| 2a | 6% | 2:1 | 0.40 | 0.1184 | no detectable odor (0 ppm) |
| 2b | 6% | 2:1 | 0.37 | 0.1126 | no detectable odor (0 ppm) |
| 3a | 8% | 2:1 | 0.42 | 0.1584 | no detectable odor (0 ppm) |
| 3b | 8% | 2:1 | 0.42 | 0.1175 | no detectable odor (0 ppm) |
| 3c | 8% | 2:1 | 0.41 | 0.1111 | no detectable odor (0 ppm) |
| 3d | 8% | 2:1 | 0.46 | 0.1534 | no detectable odor (0 ppm) |
| 3e | 8% | 2:1 | 0.45 | 0.1523 | no detectable odor (0 ppm) |
| 4a | 10% | 2:1 | 0.43 | 0.1149 | no detectable odor (0 ppm) |
| 4b | 10% | 2:1 | 0.40 | 0.1015 | no detectable odor (0 ppm) |
| 5a | 12% | 2:1 | 0.45 | 0.1044 | no detectable odor (0 ppm) |
| 5b | 12% | 2:1 | 0.38 | 0.1174 | no detectable odor (0 ppm) |
| 6a | 14% | 2:1 | 0.44 | 0.1114 | no detectable odor (0 ppm) |
| 6b | 14% | 2:1 | 0.37 | 0.1154 | no detectable odor (0 ppm) |
| 7a | 16% | 2:1 | 0.36 | 0.1171 | no detectable odor (0 ppm) |
| 7b | 16% | 2:1 | 0.45 | 0.1186 | no detectable odor (0 ppm) |
| 8a | 18% | 2:1 | 0.44 | 0.1223 | no detectable odor (0 ppm) |
| 8b | 18% | 2:1 | 0.41 | 0.1140 | no detectable odor (0 ppm) |
| 9a | 20% | 2:1 | 0.43 | 0.1214 | no detectable odor (0 ppm) |
| 9b | 20% | 2:1 | 0.44 | 0.1268 | no detectable odor (0 ppm) |
| 10a | 6% | 1:1 | 0.37 | 0.1048 | no detectable odor (0 ppm) |
| 10b | 6% | 1:1 | 0.41 | 0.1046 | no detectable odor (0 ppm) |
| 10c | 6% | 1:1 | 0.43 | 0.1218 | no detectable odor (0 ppm) |
| 10d | 6% | 1:1 | 0.41 | 0.1133 | no detectable odor (0 ppm) |
| 11a | 8% | 1:1 | 0.42 | 0.1138 | no detectable odor (0 ppm) |
| 11b | 8% | 1:1 | 0.40 | 0.1139 | no detectable odor (0 ppm) |
| 11c | 8% | 1:1 | 0.37 | 0.1144 | no detectable odor (0 ppm) |
| 11d | 8% | 1:1 | 0.37 | 0.1228 | no detectable odor (0 ppm) |
| 12a | 10% | 1:1 | 0.39 | 0.1041 | no detectable odor (0 ppm) |
| 12b | 10% | 1:1 | 0.37 | 0.1310 | no detectable odor (0 ppm) |
| 12c | 10% | 1:1 | 0.41 | 0.1084 | no detectable odor (0 ppm) |
| 12d | 10% | 1:1 | 0.38 | 0.1156 | no detectable odor (0 ppm) |
| 13a | 12% | 1:1 | 0.38 | 0.1128 | no detectable odor (0 ppm) |
| 13b | 12% | 1:1 | 0.42 | 0.1193 | no detectable odor (0 ppm) |
| 13c | 12% | 1:1 | 0.37 | 0.1149 | no detectable odor (0 ppm) |
| 13d | 12% | 1:1 | 0.38 | 0.1154 | no detectable odor (0 ppm) |
| 14 | 8% | 1:2 | 0.43 | 0.1144 | no detectable odor (0 ppm) |

Control Example 4 and Examples 15a-15c

Pad samples were prepared and artificial urine odor testing was carried out identical to Examples 3a-3e described above, except that the antimicrobial composition was coated onto the nonwoven substrate using the spray application method described above. A sample of an unmodified pad was also tested as a control. Results are provided in Table 2.

TABLE 2

| Example | Pad weight (grams) | Antimicrobial coating weight (gsm) | Odor testing-artificial urine |
|---|---|---|---|
| Control 4 | 0.47 | none | Strong ammonia odor (50 ppm) |
| 15a | 0.44 | 40 gsm | no detectable odor (0 ppm) |
| 15b | 0.40 | 40 gsm | no detectable odor (0 ppm) |
| 15c | 0.46 | 40 gsm | no detectable odor (0 ppm) |

Examples 16-28

Antimicrobial coatings were prepared using organic acids other than SA. Samples were prepared and artificial urine odor testing was carried out as described above. The amount of organic acid was either 8 weight percent or 20 weight percent and the PEG 3350:CA carrier ratio was either 2:1 or 1:1. The antimicrobial coating formulations and odor testing results are shown in Table 3.

TABLE 3

| Example | Acid type | Weight % Acid | PEG 3350:CA ratio | Pad weight (grams) | Antimicrobial coating weight (gsm) | Odor testing—artificial urine |
|---|---|---|---|---|---|---|
| 16 | Citric | 8% | 1:1 | 0.37 | 49 | no detectable odor (0 ppm) |
| 17a | Citric | 8% | 2:1 | 0.40 | 49 | no detectable odor (0 ppm) |
| 17b | Citric | 8% | 2:1 | 0.41 | 49 | no detectable odor (0 ppm) |
| 18a | Citric | 12% | 1:1 | 0.42 | 49 | no detectable odor (0 ppm) |
| 18b | Citric | 12% | 1:1 | 0.40 | 51 | no detectable odor (0 ppm) |
| 19 | Citric | 12% | 1:2 | 0.43 | 46 | some detectable odor (20-50 ppm) |
| 20a | Adipic | 8% | 2:1 | 0.48 | 51 | no detectable odor (0 ppm) |
| 20b | Adipic | 8% | 2:1 | 0.43 | 51 | no detectable odor (0 ppm) |
| 21 | Adipic | 8% | 1:1 | 0.42 | 49 | strong detectable odor (50 ppm) |
| 22 | Adipic | 8% | 1:2 | 0.37 | 50 | strong detectable odor (50 ppm) |
| 23a | 5-Chlorosalicylic | 4% | 2:1 | 0.44 | 53 | no detectable odor (0 ppm) |
| 23b | 5-Chlorosalicylic | 4% | 2:1 | 0.42 | 53 | no detectable odor (0 ppm) |
| 24a | 5-Chlorosalicylic | 6% | 2:1 | 0.39 | 51 | no detectable odor (0 ppm) |
| 24b | 5-Chlorosalicylic | 6% | 2:1 | 0.34 | 51 | no detectable odor (0 ppm) |
| 25a | 5-Chlorosalicylic | 8% | 2:1 | 0.36 | 47 | no detectable odor (0 ppm) |
| 25b | 5-Chlorosalicylic | 8% | 2:1 | 0.45 | 47 | no detectable odor (0 ppm) |
| 26a | Mandelic | 8% | 2:1 | 0.43 | 50 | no detectable odor (0 ppm) |
| 26b | Mandelic | 8% | 2:1 | 0.43 | 50 | strong detectable odor (50 ppm) |
| 27 | Mandelic | 8% | 1:1 | 0.43 | 50 | strong detectable odor (50 ppm) |
| 28 | Mandelic | 8% | 1:2 | 0.40 | 49 | strong detectable odor (50 ppm) |

Examples 29a-30b

Antimicrobial coatings were prepared using long chain (C-20 and C-22) fatty alcohols in combination with PEG 3350 as the carrier instead of CA. The amount of SA was 8 weight percent and the PEG 3350:hydrophobic carrier ratio was 2:1. The antimicrobial coating formulations and odor testing results are shown in Table 4.

TABLE 4

| Example | Hydrophobic carrier | Pad weight (grams) | Antimicrobial coating weight (gsm) | Odor testing-artificial urine |
|---|---|---|---|---|
| 29a | cis-13-Docosenol | 0.43 | 47 | no detectable odor (0 ppm) |
| 29b | cis-13-Docosenol | 0.39 | 47 | no detectable odor (0 ppm) |
| 30a | 1-Eicosanol | 0.39 | 45 | no detectable odor (0 ppm) |
| 30b | 1-Eicosanol | 0.43 | 45 | no detectable odor (0 ppm) |

Control Examples 5 and 6 and Examples 31a-32c

An antimicrobial composition identical to that used for Example 3 was prepared and pad samples were prepared as described above. These samples were evaluated for the odor control performance with the artificial menses test described above using 3 mL and 5 mL inocula. Results are shown in Table 5.

TABLE 5

| Example | Menses amount | Pad weight (grams) | Antimicrobial coating weight (gsm) | Odor testing-artificial menses |
|---|---|---|---|---|
| Control 5 | 3 mL | 0.48 | 0 | strong malodor |
| 31a | 3 mL | 0.44 | 50 | significantly less malodor than control |

TABLE 5-continued

| Example | Menses amount | Pad weight (grams) | Antimicrobial coating weight (gsm) | Odor testing-artificial menses |
|---|---|---|---|---|
| 31b | 3 mL | 0.47 | 50 | significantly less malodor than control |
| 31c | 3 mL | 0.43 | 50 | significantly less malodor than control |

TABLE 5-continued

| Example | Menses amount | Pad weight (grams) | Antimicrobial coating weight (gsm) | Odor testing-artificial menses |
|---|---|---|---|---|
| Control 6 | 5 mL | 0.42 | 0 | strong malodor |
| 32a | 5 mL | 0.39 | 50 | significantly less malodor than control |
| 32b | 5 mL | 0.41 | 50 | significantly less malodor than control |
| 32c | 5 mL | 0.42 | 50 | significantly less malodor than control |

Examples 33-36

An antimicrobial composition identical to that used for Example 3 was prepared and pad samples were prepared as described above. The weight of the antimicrobial coating on the nonwoven substrates used in preparing the pad samples was 10 gsm for Examples 33 and 35 and 50 gsm for Examples 34 and 36. The pad samples were evaluated for antimicrobial activity using the antimicrobial activity test method described above. Test results for *Staphylococcus aureus* (ATCC 6538) are provided in Table 6. Test results for *Klebsiella pneumoniae* (ATCC 4352) are provided in Table 7.

TABLE 6

| | Example 33 | Example 34 |
|---|---|---|
| Inoculated Bacteria Concentration (CFU/ml) | 2.0 + 05 | 2.0 + 05 |
| Growth Value (F) | 1.91 | 1.91 |
| Bacteriostatic Activity Value (S) | 5.24 | 5.73 |
| Bactericidal Activity Value (L) | 3.97 | 3.97 |

TABLE 7

| | Example 35 | Example 36 |
|---|---|---|
| Inoculated Bacteria Concentration (CFU/ml) | 2.0 + 05 | 2.0 + 05 |
| Growth Value (F) | 2.20 | 2.20 |
| Bacteriostatic Activity Value (S) | 5.80 | 5.80 |
| Bactericidal Activity Value (L) | 3.70 | 3.70 |

Examples 37-41

Experiments were carried out in order to determine the processability of the antimicrobial compositions using a spray applicator. Compositions like that described above for Example 3 were prepared except that various molecular weights of the PEG component of the formula were evaluated (8000 or 8K; 12000 or 12K) or small amounts of higher molecular weight PEG (400000 or 400K) were added to the formula. The compositions evaluated are provided in Table 8. Viscosity measurements were obtained for the compositions using the viscosity test described above. Results are provided in Table 9.

TABLE 8

| Example | SA (weight %) | CA (weight %) | PEG 3350 (weight %) | 400K PEG (weight %) | 8K PEG (weight %) | 12K PEG (weight %) |
|---|---|---|---|---|---|---|
| 37 | 8 | 31 | 60.5 | 0.5 | 0 | 0 |
| 38 | 8 | 31 | 60 | 1 | 0 | 0 |
| 39 | 8 | 31 | 59 | 2 | 0 | 0 |
| 40 | 8 | 31 | 0 | 0 | 61 | 0 |
| 41 | 8 | 31 | 0 | 0 | 0 | 61 |

TABLE 9

| Example | Viscosity @ 50° C. | Viscosity @ 60° C. | Viscosity @ 70° C. | Viscosity @ 80° C. | Viscosity @ 90° C. | Viscosity @ 100° C. |
|---|---|---|---|---|---|---|
| 37 | 359.0 | 217.3 | 145.9 | 116.6 | 96.1 | 77.6 |
| 38 | 568.9 | 386.4 | 265.3 | 206.5 | 162.8 | 130.7 |
| 39 | 1450 | 1132 | 893.8 | 726.9 | 604.6 | 514.8 |
| 40 | 588.7 | 432.9 | 322.6 | 248.1 | 196 | 159.3 |
| 41 | 1948 | 1415 | 1029 | 771.7 | 595.5 | 470.2 |

The ability of the compositions to be sprayed onto a nonwoven substrate was examined using the spray application procedure described above. It was observed that that the processability improved as the viscosity increased. The higher viscosity compositions allowed for the formation of cohesive fibers that improved the ability to be sprayed onto a substrate. Static pressure in the die cavity also improved with the higher viscosity compositions, which produced a uniform coating across all nozzles. Conversely, the lower viscosity compositions produced droplets which tended to either aerosolize or contaminate the surrounding area. Lower viscosity compounds also failed to provide back pressure in the die, which led the liquid to follow the path of least resistance through the die and onto the substrate, which produced uneven coatings on the substrate.

Examples 42-44

In the following examples the rate of release of the antimicrobials agent, salicylic acid, was studied. 3" circles were cut from center of a 4"×6" Wypall L30 with 50 gsm coating of the indicated compositions. The original amount of salicylic acid in the samples was 0.0182 g.

| Sample | Cetyl alcohol (%) | CARBOWAX 8000 (%) | Salicylic Acid (%) |
|---|---|---|---|
| 42 | 92 | 0 | 8 |
| 43 | 46 | 46 | 8 |
| 44 | 0 | 92 | 8 |

Samples placed into a cylindrical glass container containing 75 g distilled water. After five minute increments, the coated samples were removed and the water titrated with 0.1 N NaOH with a phenolphthalein indicator to determine the amount of salicylic acid in solution. Samples were transferred every 5 minutes into fresh 75 g DI water for a total of 5 specimens. The results are shown in Table 10

TABLE 10

| | Example | | |
|---|---|---|---|
| | 42 | 43 | 44 |
| | Composition | | |
| | A | B | C |
| Time (min) | Salicylic Acid (mg) | | |
| 5 | 3.52 | 9.32 | 12.43 |
| 10 | 4.07 | 4.49 | 4.83 |
| 15 | 2.76 | 3.11 | 1.38 |
| 20 | 2.07 | 1.38 | 0.35 |
| 25 | 1.04 | 0.69 | 0.69 |
| 30 | 0.69 | 0.69 | 0.69 |
| coating weight (gsm) | 39 | 50 | 53 |
| Total amount of SA | 17.95 | 22.86 | 24.17 |

20% of the salicylic acid in the 92% cetyl alcohol composition is released in the first five minutes. 51% of the salicylic acid in the 92% PEG 3350 composition is released in the first five minutes. For a 50 gsm coating and 1% and 20% SA, a 0.6 to 19 mg/min release could be obtained.

Example 45

The performance of a disposable article containing a color change indicator and an antimicrobial composition coated on a nonwoven sheet was evaluated. A small strip of pH color indicating paper (available from EMD Chemicals, Gibbstown, N.J. under the trade designation "COLOR-pHAST pH 4.0-7.0") was used as the color change indicator. A small piece of a nonwoven sheet (Wypall L30 tissue) coated at 50 gsm with an antimicrobial composition containing SA (8 weight percent) and PEG (MW=8000):CA carrier (2:1 weight percent ratio) was inserted between the absorbent core and the acquisition distribution layer (ADL) of a feminine hygiene pad (available from Kimberly Clark Corporation, Dallas, Tex., under the trade designation "KOTEX OVERNIGHT MAXI WITH WINGS"). A small strip of the pH color indicating paper was placed directly on top of the inserted nonwoven sheet (i.e. placed between the coated nonwoven sheet and the ADL). In the same manner as with the coated sheet, an uncoated piece of the nonwoven sheet with a strip of pH color indicating paper placed on top was inserted in a separate location in the pad. The uncoated sheet served as an experimental control.

Water was applied to the topsheet of the pad in an amount sufficient to saturate the areas of the pad where the pH color indicating strips were located. A minimum amount of hand pressure was applied to the topsheet of the pad to distribute the liquid and to simulate the compression that occurs during wear. After a few minutes, the pH color indicating paper located above the tissue coated with the antimicrobial composition changed from a green to an orange color. The pH color indicating paper located above the uncoated tissue maintained its original green color. The color change was clearly visible when viewing through the topsheet of the pad and provided a positive indication that the SA component of the antimicrobial composition was released into the applied fluid.

The same color change results were observed in a configuration where an additional piece of uncoated tissue was placed between the coated tissue and the pH color indicating paper.

The invention is further represented by the following embodiments.
1. An antimicrobial composition comprising:
    a) a carrier comprising fatty alcohol and a poly(alkyleneoxy) polymer, and
    b) an antimicrobial agent.
2. The antimicrobial composition of embodiment 1 having a melting point of 50° C. or greater.
3. The antimicrobial composition of embodiment 1 or 2 wherein the antimicrobial agent is an antimicrobial organic acid selected from α- and β-hydroxy acids.
4. The antimicrobial composition of embodiment 3 wherein the antimicrobial acid is selected from benzoic acids and hydroxybenzoic acids.
5. The antimicrobial composition of any of the previous embodiments comprising 1 to 20 wt. % of the antimicrobial agent, relative to the total weight of the composition.
6. The antimicrobial composition of embodiment 3 wherein the α-hydroxy acid is selected from lactic acid, malic acid, citric acid, 2-hydroxybutanoic acid, 3-hydroxybutanoic acid, mandelic acid, gluconic acid, glycolic acid, tartaric acid, alpha-hydroxyethanoic acid, ascorbic acid, alpha-hydroxyoctanoic acid, hydroxycaprylic acid, and salicylic acid.
7. The antimicrobial composition of embodiment 3 wherein the β-hydroxy acid is selected from salicylic acid, beta-hydroxybutanoic acid, tropic acid, and trethocanic acid.
8. The antimicrobial composition of any of the previous embodiments further comprising a surfactant.
9. The antimicrobial composition of any of the previous embodiments wherein poly(alkyleneoxy) polymer is a poly(ethyleneoxy) polymer.
10. The antimicrobial composition of any of the previous embodiments wherein poly(alkyleneoxy) polymer has a melting point of at least 50° C.
11. The antimicrobial composition of any of the previous embodiments wherein the fatty alcohol is a $C_{14}$-$C_{22}$ fatty alcohol.
12. The antimicrobial composition of any of the previous embodiments wherein the fatty alcohol has a melting point of at least 50° C.
13. The antimicrobial composition of any of the previous embodiments comprising:
    a) 80 to 99 wt. % of a carrier comprising a fatty alcohol and a poly(alkyleneoxy) polymer, wherein the fatty alcohol comprises at least 10 wt. % of the carrier; and
    b) 1 to 20 wt. %, of an antimicrobial agent, based on the total weight of the composition.
14. The antimicrobial composition of embodiment 13 comprising:
    a) 90 to 95 wt. % of a hydrophilic carrier comprising fatty alcohol and a poly(alkyleneoxy) polymer, wherein the fatty alcohol comprises at least 20 wt. % of the hydrophilic carrier; and
    b) 5 to 10 wt. % of an antimicrobial agent, based on the total weight of the composition.
15. The composition of any of the previous embodiments which is a homogenous solution at temperatures above the melt temperature.
16. The composition of any of the previous embodiments comprising less than 1 wt. % of esters of the fatty alcohol.

17. The composition of any of embodiments 1-3, 6, and 8-16 wherein the antimicrobial acid is an alpha-hydroxy acid of the formula:

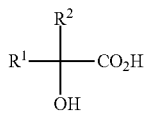

wherein $R^1$ and $R^2$ are each independently H or a $C_1$-$C_8$ alkyl group, a $C_6$-$C_{12}$ aryl, or a $C_6$-$C_{12}$ aralkyl or alkaryl group.

18. The composition of any of embodiments 1-3, 4, and 7-16 wherein the antimicrobial acid is of the formulas:

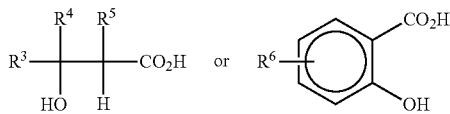

wherein: $R^3$, $R^4$, and $R^5$ are each independently H or a $C_1$-$C_8$ alkyl group, $C_6$-$C_{12}$ aryl, or $C_6$-$C_{12}$ aralkyl or alkaryl group; and $R^6$ is H, $(C_1$-$C_4)$alkyl or a halogen.

19. The composition of any of the previous embodiments wherein the antimicrobial agent is an antimicrobial acid of the formula:

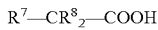

wherein: $R^7$ and $R^8$ are each independently H or a $C_1$-$C_4$ alkyl group, a $C_6$-$C_{12}$ aryl group, a $C_6$-$C_{12}$ group containing both aryl groups and alkyl groups and $R^7$ and $R^8$ may be optionally substituted with one or more carboxylic acid groups.

20. The antimicrobial composition of any of the previous embodiments, wherein the carrier is hydrophilic.

21. The antimicrobial composition of any of the previous embodiments wherein the antimicrobial agent is selected from phenolic compounds.

22. The antimicrobial composition of any of the previous embodiments wherein the antimicrobial agent is selected from biguanide compounds.

23. The antimicrobial composition of any of the previous embodiments, wherein the rate of release of the antimicrobial agent in an aqueous solution may be varied by varying the ratio of the fatty alcohol and the poly(alkyleneoxy) polymer.

24. A disposable absorbent article comprising a coating of the antimicrobial composition of any of the previous embodiments on a surface of the disposable article.

25. The disposable absorbent article of embodiment 24 comprising a topsheet, a backsheet joined to the topsheet, a absorbent material disposed between the topsheet and the backsheet, and a coating of the antimicrobial composition disposed on at least one surface of the topsheet, the backsheet, the absorbent material or other component surface of the disposable article.

26. The disposable absorbent article of any of the previous embodiments 24-25 wherein the disposable absorbent article is a woven, nonwoven, or knitted wipe.

27. The disposable absorbent article of any of the previous embodiments 24-25 wherein the disposable absorbent article is selected from disposable infant diapers, sanitary napkins, panty liners and tampons, products for adult incontinence, personal care wipes, wound dressings, bandages, and household wipes.

28. The disposable absorbent article of any of the previous embodiments 24-27 wherein the coating weight of the antimicrobial composition is of 0.5-25 g/sq meter.

29. The disposable absorbent article of any of the previous embodiments 24-28 wherein the antimicrobial composition is applied from the melt.

30. The disposable absorbent article of embodiment 29 wherein the viscosity of the melt is 100 to 3000 centipoise.

31. The antimicrobial composition of any of embodiments 1-23 further comprising a visual indicator.

32. The antimicrobial composition of embodiment 31 wherein the visual indicator is a wetness indicator.

33. The disposable article of any of embodiments 24-30 further comprising a visual indicator.

34. A method of making a disposable article having an antimicrobial coating comprising the steps of providing a disposable article and coating the antimicrobial composition of any of embodiments 1-23 on at least one surface of the disposable article.

What is claimed is:

1. A method of making a disposable article comprising applying a molten antimicrobial composition on at least one surface of a disposable article such that the antimicrobial composition is within the disposable article, wherein the molten antimicrobial composition comprises (1) a carrier comprising a fatty alcohol and a poly(alkyleneoxy) polymer and (2) an antimicrobial agent consisting of a beta-hydroxyl acid or a mixture of beta-hydroxyl acids.

2. The method of claim 1 comprising the steps of providing a topsheet, backsheet, and absorbent material;
applying the antimicrobial composition on at least one surface of the disposable article such that the antimicrobial composition is between the topsheet and the backsheet;
disposing the absorbent material between the topsheet and the backsheet; and
joining the topsheet and backsheet.

3. The method of claim 2 wherein the absorbent material is a fibrous absorbent material.

4. The method of claim 2 wherein the step of applying the antimicrobial composition comprises applying the antimicrobial composition to
a) a body facing surface of the backsheet,
b) a body facing surface of the absorbent material,
c) a garment facing surface of the absorbent material,
d or
a combination thereof.

5. The method of claim 1 comprising applying the antimicrobial composition such that the coating weight ranges from 0.5-25 g/sq meter.

6. The method of claim 1 wherein the antimicrobial composition has a melting point of 50° C. or greater.

7. The method of claim 1 wherein the antimicrobial composition has a rate of release in water ranging from 0.1 to 50 mg/minutes.

8. A disposable article comprising an antimicrobial composition within the disposable article, wherein the antimicrobial composition comprises (1) a carrier comprising a fatty alcohol and a poly(alkyleneoxy) polymer and (2) an antimicrobial agent consisting of a beta-hydroxyl acid or a mixture of beta-hydroxyl acids.

9. The disposable article of claim 8 wherein the antimicrobial composition comprises 1 to 20 wt-% of the antimicrobial agent.

10. The disposable article of claim 8 wherein the beta-hydroxyl acid is of the formulas:

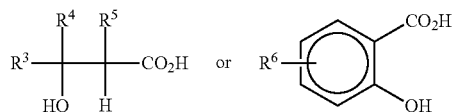

wherein: $R^3$, $R^4$, and $R^5$ are each independently H or a $C_1$-$C_8$ alkyl group, $C_6$-$C_{12}$ aryl, or $C_6$-$C_{12}$ aralkyl or alkaryl group; and $R^6$ is H, ($C_1$-$C_4$) alkyl or a halogen.

11. The disposable article of claim 8 wherein the antimicrobial composition further comprises a visual indicator.

12. The disposable article of claim 8 wherein the disposable absorbent article is selected from disposable infant diapers, sanitary napkins, panty liners and tampons, products for adult incontinence, personal care wipes, wound dressings, bandages, and household wipes.

13. The disposable article of claim 8 wherein the poly(alkyleneoxy) polymer is a poly(ethyleneoxy) polymer.

14. The disposable article of claim 8 wherein the antimicrobial composition is disposed at a surface selected from:
a) a body facing surface of the backsheet,
b) a body facing surface of the absorbent material,
c) a garment facing surface of the absorbent material,
d or
a combination thereof.

15. The disposable article of claim 8 wherein the antimicrobial composition is disposed at a coating weight that ranges from 0.5-25 g/sq meter.

16. The disposable article of claim 8 wherein the antimicrobial composition has a melting point of 50° C. or greater.

17. The disposable article of claim 8 wherein the antimicrobial composition has a rate of release in water ranging from 0.1 to 50 mg/minutes.

* * * * *

UNITED STATES PATENT AND TRADEMARK OFFICE
CERTIFICATE OF CORRECTION

| | | |
|---|---|---|
| PATENT NO. | : 9,522,211 B2 | Page 1 of 2 |
| APPLICATION NO. | : 14/481190 | |
| DATED | : December 20, 2016 | |
| INVENTOR(S) | : David Amos | |

It is certified that error appears in the above-identified patent and that said Letters Patent is hereby corrected as shown below:

In the Specification

Column 6
Line 3, Delete "N60K"" and insert -- N60K --, therefor.
Line 41, Delete "melt-processable" and insert -- melt-processible --, therefor.

Column 8
Line 62, Delete "dimethyldiallylammonium" and insert -- dimethyldialkylammonium --, therefor.

Column 9
Line 27 (Approx.), Delete "Aveci," and insert -- Avicii, --, therefor.
Line 37 (Approx.), After "hydrochloride" insert -- . --.

Column 10
Line 40, Delete "pyoverdin," and insert -- pyoverdine, --, therefor.

Column 11
Line 55, Delete "such" and insert -- Such --, therefor.

Column 16
Line 1, After "napkin)" insert -- . --.
Line 67, After "article" insert -- . --.

Column 17
Line 30, Delete "flouropolymers" and insert -- fluoropolymers --, therefor.

Column 18
Line 9, Delete "and or" and insert -- and/or --, therefor.
Line 26, Delete "and or" and insert -- and/or --, therefor.

Signed and Sealed this
Second Day of May, 2017

Michelle K. Lee
*Director of the United States Patent and Trademark Office*

CERTIFICATE OF CORRECTION (continued)
U.S. Pat. No. 9,522,211 B2

Column 21
Line 34, After "shake-out" insert -- . --.

Column 28
Line 35, Delete "that that" and insert -- that --, therefor.

Column 29
Line 3, After "10" insert -- . --.

In the Claims

Column 32
Line 49, In Claim 4, delete "d" and insert -- d) --, therefor.

Column 34
Line 8, In Claim 14, delete "d" and insert -- d) --, therefor.